(12) United States Patent
Hart et al.

(10) Patent No.: US 12,291,637 B2
(45) Date of Patent: May 6, 2025

(54) ACIDIC BONDING COMPOSITIONS AND METHODS FOR RESTORING AND COLOR TONING LIGHTENED HAIR

(71) Applicant: L'OREAL, Paris (FR)

(72) Inventors: Taylor Katherine Hart, New York, NY (US); Kimberly Christine Dreher, Brielle, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 17/957,707

(22) Filed: Sep. 30, 2022

(65) Prior Publication Data

US 2024/0124708 A1  Apr. 18, 2024

(51) Int. Cl.
| | |
|---|---|
| *C08L 71/02* | (2006.01) |
| *A61K 8/37* | (2006.01) |
| *A61K 8/44* | (2006.01) |
| *A61K 8/46* | (2006.01) |
| *A61K 8/73* | (2006.01) |
| *A61Q 5/00* | (2006.01) |
| *A61Q 5/06* | (2006.01) |

(52) U.S. Cl.
CPC ............... *C08L 71/02* (2013.01); *A61K 8/37* (2013.01); *A61K 8/44* (2013.01); *A61K 8/466* (2013.01); *A61K 8/731* (2013.01); *A61Q 5/004* (2013.01); *A61Q 5/065* (2013.01); *A61K 2800/30* (2013.01); *A61K 2800/432* (2013.01); *A61K 2800/48* (2013.01); *A61K 2800/51* (2013.01); *A61K 2800/524* (2013.01)

(58) Field of Classification Search
CPC .. C08L 71/02; A61K 8/37; A61K 8/44; A61K 8/466; A61K 8/731; A61K 2800/30; A61K 2800/432; A61K 2800/48; A61K 2800/51; A61K 2800/524; A61Q 5/004; A61Q 5/065
See application file for complete search history.

(56) References Cited

U.S. PATENT DOCUMENTS

| | | | |
|---|---|---|---|
| 11,660,260 B2 | 5/2023 | Xavier et al. | |
| 2020/0197283 A1* | 6/2020 | Zhang | A61K 8/4926 |
| 2021/0267868 A1* | 9/2021 | Xavier | A61K 8/604 |
| 2022/0249333 A1 | 8/2022 | Hasegawa | |
| 2023/0099740 A1* | 3/2023 | Hart | A61K 8/375 424/70.13 |

FOREIGN PATENT DOCUMENTS

| | | | | |
|---|---|---|---|---|
| CA | 2040963 A1 | * | 10/1991 | |
| EP | 4018994 A1 | * | 6/2022 | ........... A61K 8/0229 |
| FR | 3013590 A1 | * | 5/2015 | ............... A61K 8/19 |
| FR | 3108845 A1 | | 10/2021 | |
| FR | 3114971 A1 | | 4/2022 | |
| WO | WO-2021121823 A1 | * | 6/2021 | ............... A61K 8/19 |
| WO | 2021173614 A1 | | 9/2021 | |

OTHER PUBLICATIONS

Machine translation for patent FR3013590A1; published May 2015 (Year: 2015).*
Machine translation for patent FR3013590A1 (Year: 2015).*
Machine translation for patent WO2021121823A1 (Year: 2021).*
Anonymous, Mintel, "Triple Care Hair Colourant," XP93057729, No. 8638965, Apr. 20, 2021, www.gnpd.com.
Anonymous, Mintel, "Tinting pH Acidifier," XP93057733, No. 8409037, Jan. 14, 2021, www.gnpd.com.
Anonymous, Mintel, "Intensive Toning Hair Mask," XP093057637, No. 9825142, Aug. 18, 2022, www.gnpd.com.
Anonymous, Mintel, "Strengthening Shampoo," XP093057629, No. 8921071, Aug. 4, 2021, www.gnpd.com.
Search Report issued to French counterpart Application No. FR2212420 dated Jun. 27, 2023.

* cited by examiner

*Primary Examiner* — Robert A Wax
*Assistant Examiner* — John W Lippert, III
(74) *Attorney, Agent, or Firm* — McNees Wallace & Nurick LLC

(57) ABSTRACT

A hair refreshing composition that accomplishes neutralizing and/or toning in 5 minutes and includes a color toning system with least one violet toned direct dye, and an acidic bonding restorative base that includes least one anionic surfactant including an isethionate surfactant, at least one ester including coco-caprylate/caprate, at least one cationic compound, at least one additional surfactant, and a cosmetically acceptable solvent that includes water. The composition confers the dual benefits of restoring hair texture and toning and/or neutralizing hair color, particularly in lightened or color lifted blonde hair in a formulation that is stable (retention of viscosity, bulk tone and efficacy of toning/neutralizing brassiness).

20 Claims, 1 Drawing Sheet

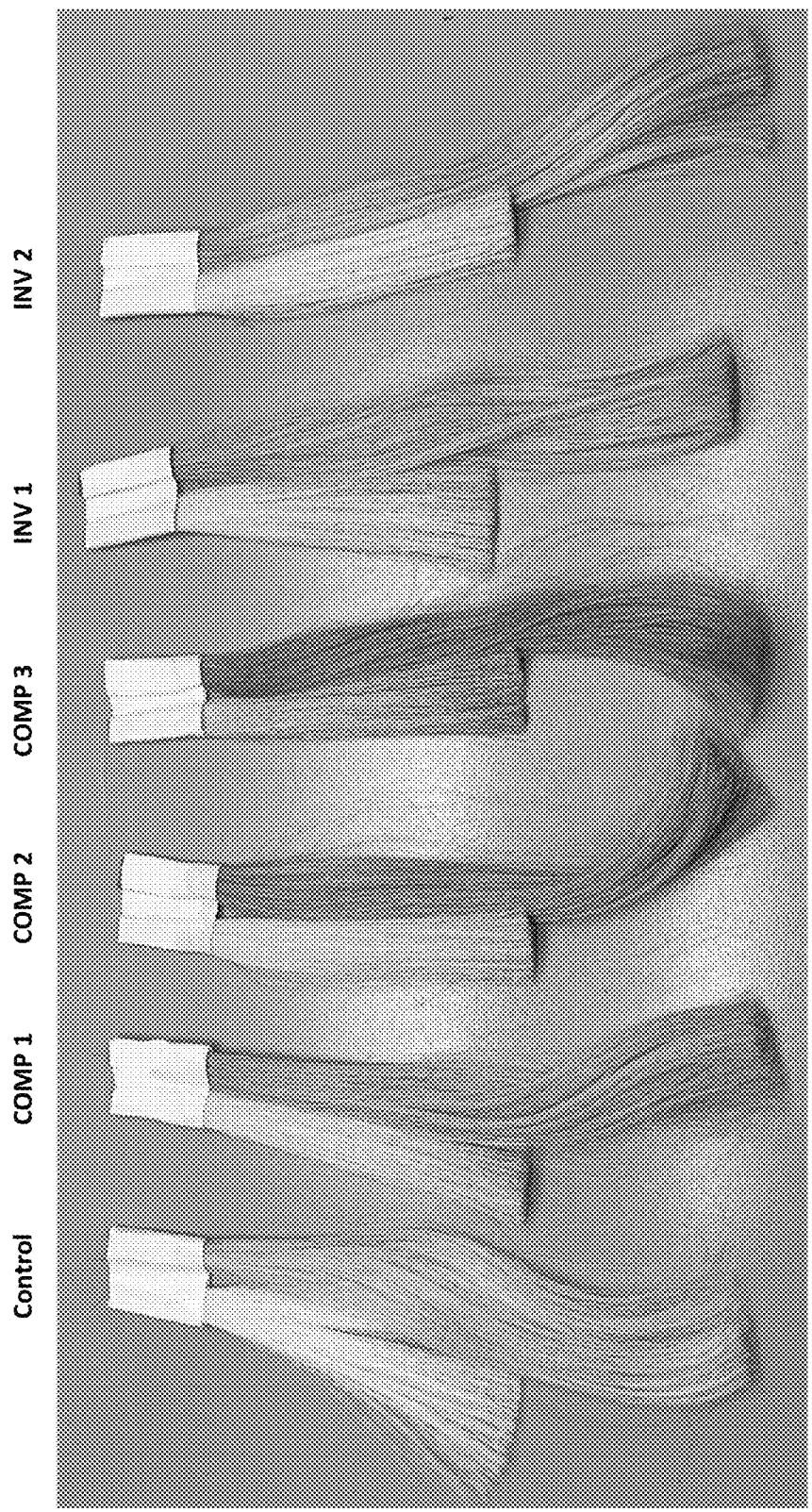

ACIDIC BONDING COMPOSITIONS AND METHODS FOR RESTORING AND COLOR TONING LIGHTENED HAIR

TECHNICAL FIELD

The disclosure relates to compositions and methods for treating keratinous substrates, such as skin, hair, and/or scalp, and in particular for restoring and color toning lightened keratinous substrates. The hair refreshing composition may be rinse-off compositions containing an acidic bonding restorative base and a color toning system, such as a rinse-off treatment, shampoo or cleanser. The methods may comprise employing an acidic bonding and toning compositions to restore and color tone lightened keratinous substrates and/or conditioning the skin, hair, and/or scalp.

BACKGROUND

Consumers desire healthy skin and healthy, strong hair, as healthy-looking skin and hair is considered to be a sign of good health and good hygiene. Consumers who choose to employ lightening agents for keratinous tissues, such as use of bleaching agents to lighten hair, often experience damage and dryness and unwanted color/tone qualities in the hair. When a bleaching treatment is applied, it is common for the hair to become weak due to the breakage of bonds in the hair fibers. In addition, lightening can result the natural undertone of the consumer's hair becoming more pronounced. Particularly in the case of blonde consumers, the undertones, or unwanted warm tones, cause what referred to as "brassiness." In order to neutralize the damage to hair, bonding repairing treatments are used, and to neutralize brassiness, toning compositions can be applied. Unfortunately, bond repairing compositions are not suitable for providing the benefits of color toning to neutralize brassiness associated with lightening. Thus, routines for treating lightened hair typically require multiple steps of treatment after lightening, often requiring visits to a professional hairdresser to sequentially apply different compositions to accomplish bond repair and color toning. Such routines can be inefficient and expensive. Attempts to reduce the routine to a single step by mixing the treatments are generally not successful because a direct mixing of the bonding and toning compositions can result in diminished effectiveness of one or both due to incompatibility of the respective components.

Consumers perceive a need for a composition that repairs damaged hair and addresses brassiness. Such a composition must not demonstrate diminished performance in restorative and/or color toning and/or neutralizing benefits as compared with two step treatment routines, and must have stability to be viable for shelf storage and consumer use and must have excellent aesthetic properties. Such a composition must thus include the appropriate combination and proportions of bond repairing and color toning components to provide excellent restorative properties that confer moisturizing, detangling, shine, and smoothness to the hair while also providing excellent color refreshing to tone and/or neutralize brassiness and thus enable the consumer to achieve the desired color and brightness.

The present disclosure addresses the consumer needs and performance requirements in the provided hair refreshing composition and method for refreshing the skin, hair, and/or scalp, wherein the hair refreshing composition may be used in a single step to provide surprisingly effective color toning and/or neutralizing benefits and a bonding benefit that consumers associate with healthy hair, along with good foaming, lather, and distribution on application and physical and chemical stability.

SUMMARY

According to various embodiments, the disclosure provides a hair refreshing composition comprising a color toning system comprising at least one direct dye, and an acidic bonding restorative base, wherein the acidic bonding restorative base comprises at least one anionic surfactant comprising an isethionate surfactant, at least one ester comprising coco-caprylate/caprate, at least one cationic compound, at least one additional surfactant selected from the group consisting of non-ionic surfactants, amphoteric surfactants and combinations thereof, and a cosmetically acceptable solvent comprising water.

In some embodiments, the one or more direct dyes is present in the hair refreshing composition from about 0.0001% to 10% by weight based on the total weight of the hair refreshing composition.

In some particular embodiments, the one or more direct dyes comprises a violet toned direct dye.

In some particular embodiments, the violet toned direct dye consists of the direct dye EXT. VIOLET 2 and is present in the hair refreshing composition from about 0.1% to about 2%. In some particular embodiments, the violet toned direct dye consists of the direct dye EXT. VIOLET 2 and is present in the hair refreshing composition from about 0.5% to about 1.0% by weight based on the total weight of the hair refreshing composition.

In some specific embodiments, the hair refreshing composition excludes HC VIOLET NO. 2, BASIC VIOLET 2, HC BLUE NO. 2, BASIC RED 51, or combinations thereof. In some specific embodiments, the hair refreshing composition excludes each of HC VIOLET NO. 2, BASIC VIOLET 2, HC BLUE NO. 2, and BASIC RED 51.

According to some embodiments, the hair refreshing composition includes direct color dyes for violet tones that are provided in varied concentrations that achieve a consumer's desired cosmetic shade effect with a processing time of about 5 minutes and that demonstrate stability.

In some embodiments, the composition comprises at least one non-ionic or amphoteric surfactant selected from the group consisting of alkyl polyglucosides, monounsaturated glyceryl esters, betaines, sultaines, amphoacetates, amphopropionates, and combinations thereof.

In some embodiments, the composition comprises at least one non-ionic surfactant comprising one or more alkyl polyglucosides selected from the group consisting of lauryl glucoside, octyl glucoside, decyl glucoside, coco glucoside, caprylyl/capryl glucoside, and sodium lauryl glucose carboxylate, and combinations thereof, or one or more monounsaturated glyceryl esters selected from the group consisting of glyceryl behenate, glyceryl caprate, glyceryl cocoate, glyceryl erucate, glyceryl hydroxystearate, glyceryl isostearate, glyceryl lanolate, glyceryl laurate, glyceryl linoleate, glyceryl myristate, glyceryl oleate, glyceryl palmitate lactate, glyceryl sesquioleate, glyceryl stearate, glyceryl stearate citrate, glyceryl stearate lactate, or mixtures thereof. In certain embodiments, the at least one monounsaturated glyceryl ester may be chosen from polyglyceryl-4 isostearate, polyglyceryl-3 oleate, polyglyceryl-2 sesquioleate, triglyceryl diisostearate, diglyceryl monooleate, tetraglyceryl monooleate, and combinations thereof, or a combination thereof.

In some embodiments, the composition comprises at least one amphoteric surfactant selected from the group consisting of coco betaine, cocoamidopropyl betaine, lauryl betaine, laurylhydroxy sulfobetaine, lauryldimethyl betaine, cocoamidopropyl hydroxysultaine, behenyl betaine, capryl/capramidopropyl betaine, lauryl hydroxysultaine, stearyl betaine, and combinations thereof.

In some embodiments, the composition comprises at least one cationic compound selected from the group consisting of cationic amine-based compounds, quaternary ammonium-based compounds, cationic cellulose-based compounds, cationic starch-based compounds, cationic galactomannan compounds, cationic silicone compounds, and combinations thereof.

In some embodiments, the composition comprises at least one cationic compound selected from the group consisting of cationic guar, Polyquaternium-10, Polyquaternium-67, and combinations thereof.

In some embodiments, the composition comprises at least one emulsifier selected from the group consisting of ricinoleic acid, glycerol monostearate, glycol distearate, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, PEG-150 distearate, PEG-55 propylene glycol oleate, and combinations thereof.

In some embodiments, the composition comprises at least one polymeric thickener selected from the group consisting of carbomer, acrylates/beheneth-25 methacrylate copolymer, acrylates/C10-30 alkyl acrylate crosspolymer, ammonium polyacryloyldimethyl taurate, ammonium acryloyldimethyltaurate/steareth-25 methacrylate crosspolymer, and polyacrylate crosspolymer-6, xanthan gum, hydroxypropyl guar, *Ceratonia siliqua* (carob) gum, and combinations thereof.

In some embodiments, the composition comprises at least one additional compound selected from the group consisting of pH adjuster, chelating agent, alcohol, antimicrobial/preservative, vitamins, fragrance, humectants, emulsifiers, and combinations thereof.

In some embodiments, the hair refreshing composition is free or essentially free of imidazolium-based compounds, ammonium-based compounds, and combinations thereof. In some particular embodiments the hair refreshing composition is free or essentially free of tributylmethyl ammonium, butyl-3-methylimidazolium octyl sulfate, butyl-3-methylimidazolium acetate, ethyl-3-methylimidazolium ethylsulfate, 1,3-ethyl imidazolium acetate, and combinations thereof.

In other embodiments, the disclosure provides a hair refreshing composition comprising a color toning system comprising at least one violet toned direct dye, and an acidic bonding restorative base, wherein in the color toning system the one or more violet toned direct dyes is present from about 0.1% to about 2% by weight based on the total weight of the hair refreshing composition, and the acidic bonding restorative base comprises (a) at least one anionic surfactant selected from the group consisting of sodium cocoyl isethionate, sodium lauroyl isethionate, and combinations thereof present from about 4% to about 15% by weight, based on the total weight of the hair refreshing composition, (b) one or more additional surfactants, (c) at least one ester comprising coco-caprylate/caprate present from about 0.01% to about 5% by weight, based on the total weight of the hair refreshing composition, (d) at least one cationic compound selected from the group consisting of polysaccharide-based cationic compounds, cationic silicone compounds, and combinations thereof, (e) at least one additional surfactant chosen from non-ionic and amphoteric surfactants and comprising (i) at least one non-ionic surfactant comprising at least one alky polyglucoside present from about 7% to about 15% by weight, based on the total weight of the hair refreshing composition, and (ii) at least one amphoteric surfactant present from about 0.01% to about 7% by weight, based on the total weight of the hair refreshing composition, (f) at least one emulsifier, and (g) at least one cosmetically acceptable solvent comprising water.

In still further embodiments, the disclosure provides a method for refreshing hair. The method comprises: contacting hair with a composition comprising a color toning system comprising at least one direct dye, and an acidic bonding restorative base, wherein in the color toning system each of the one or more direct dyes is present from about 0.0001% to 10% by weight based on the total weight of the hair refreshing composition, and the acidic bonding restorative base comprises at least one anionic surfactant comprising an isethionate surfactant, at least one ester comprising coco-caprylate/caprate, at least one cationic compound, at least one additional surfactant selected from the group consisting of non-ionic surfactants, amphoteric surfactants and combinations thereof, and at least one cosmetically acceptable carrier comprising water, wherein the hair has been pre-dyed or pre-lightened.

In some embodiments, the hair is blonde hair and has been pre-lightened to a lifting level of up to 7.

In still further embodiments, the disclosure provides a process for altering the appearance of hair, the process comprising: (a) providing at least one hair refreshing composition for neutralizing or toning and bonding color treated hair, said composition comprising (i) a color toning system comprising at least one violet toned direct dye and (ii) an acidic bonding restorative base comprising at least one anionic surfactant comprising an isethionate surfactant, at least one ester comprising coco-caprylate/caprate, at least one cationic compound, at least one additional surfactant selected from the group consisting of non-ionic surfactants, amphoteric surfactants and combinations thereof, and water; (b) contacting hair with the composition in (a) to form treated hair; and (c) rinsing the treated hair, wherein the at least one hair refreshing composition includes the at least one violet toned direct dye present at a concentration selected to achieve a consumer's desired cosmetic shade effect with a processing time of about 5 minutes, and wherein the at least one hair refreshing composition that demonstrates stability.

In some embodiments, the process further includes at least one color treatment step prior to providing the at least one hair refreshing composition, wherein the hair is dyed or lightened.

In some embodiments, the hair is blonde hair and wherein the violet toned direct dye is EXT. VIOLET 2 present in the hair refreshing composition from about 0.1% to about 2% by weight based on the weight of the composition.

DESCRIPTION OF THE DRAWINGS

FIG. 1 is a photographic image showing hair swatches treated with control, comparative and inventive compositions according to the disclosure.

The detailed description set forth below in connection with the appended drawings, where like numerals reference like elements, is intended as a description of various embodiments of the disclosed subject matter and is not intended to represent the only embodiments. The embodiments described in this disclosure are provided merely as examples or illustrations and should not be construed as preferred or advantageous over other embodiments. The illustrative examples provided herein are not intended to be exhaustive or to limit the claimed subject matter to the exact forms disclosed.

DESCRIPTION

It has now been surprisingly and unexpectedly discovered that combining an acidic bonding restorative base and a color toning system provides a stable and aesthetically pleasing restorative color toning hair refreshing composition that confers the dual benefits of restoring hair texture by repairing damaged or broken bonds and toning and/or neutralizing hair color, particularly in lightened or color lifted blonde hair. The hair refreshing compositions surprisingly provides for rapid processing of about 5 minutes to provide the dual benefits of restoring and neutralizing. Moreover, the composition demonstrates stability of coloring effect and of the composition, including bulk tone and viscosity, over time and at a wide range of temperatures for up to at least 8 weeks or longer.

The hair refreshing composition may be included in a rinse-off skin or hair composition, such as, for example, a rinse-off skin cleanser or a shampoo composition. The hair refreshing composition, in which the color toning system comprises a violet direct dye, and method are particularly useful for blonde hair tones and particularly following color lightening treatments. According to certain exemplified embodiments, the color toning system is particularly useful for providing violet toning and optionally violet coloring to offset brassy yellow undertones to confer a more natural toned hair color or a more vibrant violet toned hair color according to the preference of the consumer. According to certain exemplified embodiments, the hair refreshing composition may have a bulk tone that is violet.

According to various embodiments, the disclosure provides a hair refreshing composition comprising a color toning system comprising at least one direct dye, and an acidic bonding restorative base, wherein the acidic bonding restorative base comprises at least one anionic surfactant comprising an isethionate surfactant, at least one ester comprising coco-caprylate/caprate, at least one cationic compound, at least one additional surfactant selected from the group consisting of non-ionic surfactants, amphoteric surfactants and combinations thereof, and a cosmetically acceptable solvent comprising water.

In some embodiments, the one or more direct dyes is present in the hair refreshing composition from about 0.0001% to 10% by weight based on the total weight of the hair refreshing composition. In some particular embodiments, the one or more direct dyes comprises a violet toned direct dye. In some particular embodiments, the violet toned direct dye consist of the direct dye EXT. VIOLET 2 present in the hair refreshing composition from about 0.5% to 1.0% by weight based on the total weight of the hair refreshing composition.

According to some embodiments, the hair refreshing composition includes direct color dyes for violet tones that are provided in varied concentrations that achieve a consumer's desired cosmetic shade effect with a processing time of about 5 minutes and that demonstrates stability.

In some embodiments, the inventive compositions are provided with a concentration that can be selected from at least two different concentrations of the direct dye EXT. VIOLET 2 present in the hair refreshing composition from about 0.5% to 1.0%, wherein at one concentration, hair may be neutralized to accomplish a generally natural tone of the user, while at another concentration, hair may be toned to accomplish a violet hued tone that is generally not the natural tone of the user.

The acidic bonding restorative base according to the disclosure may be a rinse-off composition such as a skin-cleansing composition or a shampoo composition. Accordingly, the acidic bonding restorative base comprises components that are traditional or useful for repairing bonds and restoring the desirable properties of hair that are damaged by coloring and lighting processes, and, in addition to the repairing and restorative components, also include components traditionally included in rinse-off compositions.

The inventors have provided a composition that confers surprisingly effective benefits that include the dual benefits of restoring hair texture by repairing damaged or broken bonds and toning and/or neutralizing hair color, particularly in lightened or color lifted blonde hair in a formulation that is physically stable as demonstrated by retention of viscosity upon formulation and over time, and is chemically stable as demonstrated by retention of bulk tone over time, and retention of efficacy of toning/neutralizing brassiness. Referring to the exemplified inventive and comparative compositions shown in the examples herein, the comparative compositions are inferior to the inventive hair refreshing composition because when tested they demonstrate one or more of the following failures: demonstrate chemical instability as evidenced by insufficient tone neutralization of brassiness when applied to blonde hair indicating that the efficacy of the color toning system is diminished; demonstrate chemical instability as evidenced by change in bulk tone over time indicating a change in the chemistry of the color toning system; demonstrate physical instability as evidenced by a drop in viscosity or a "break" in the formulation structure; and combinations of these.

The following terms are used herein to describe the inventive compositions.

As used herein, the term "keratinous substrate" is intended to include skin and hair.

The hair refreshing composition described throughout this disclosure may be a rinse-off composition. As used herein, the term "rinse-off" (also called rinse-out) refers to a composition that is applied to the skin, hair, and/or scalp and subsequently rinsed, optionally after a period of time, such as after about 5 seconds, after about 10 seconds, after about 20 seconds, after about 30 seconds, after about 1 minute, after about 5 minutes, after about 10 minutes, after about 20 minutes, after about 30 minutes, or after about an hour. In contrast, the term "leave-on" refers to a composition which is applied and is not removed by wiping or rinsing with water. According to some embodiments, the inventive hair refreshing composition is applied and subsequently rinsed off after about 5 minutes.

The term "physically stable" as used in reference to the structural or solubility state of the ingredients of the hair refreshing composition means that the hair refreshing composition lacks separation, thinning or breaking of its viscosity and overall lack of any crystal formation that is visible to the naked eye (though it may be aided by conventional corrective glasses or contact lenses or a low power magnification), over a period of time, for example immediately after the composition is mixed, or for longer periods of time, such as for one, two or four or five days, or for a period of one or more weeks, and for example up to eight (8) weeks, and at an ambient temperature from about 25° C. up to about 37° C., and after freeze thaw cycles from −20° C. through 20° C. The term "stable" as used in reference to the pH the hair refreshing composition means that the pH does not increase appreciably over time, for example as described in the examples herein. Generally, the pH of the inventive compositions is generally in a range from 5 to about 6, and in some particular embodiments from about 5.2 to about 6, and in some embodiments about 5.6+/−0.3. The term "chemically stable" as used in reference to the refreshing composition means that the bulk tone does not appreciably change over time and that the efficacy of the color toning system is not diminished over time, based on the visualization, time and ambient conditions identified herein above.

The term "bulk tone" as used herein refers to the visually perceptible (without the aid of a microscope or specialized equipment but with or without the aid of common corrective glasses or contacts) coloration of a composition.

The term "level of lifting" as used herein refers to a standard generally understood in the keratinous tissue coloring industry to reflect the level of lightening achieved by a lifting or bleaching composition. As used herein with reference to the exemplified tested compositions, the level of lifting employed is "level 7" commonly associated with lightening of blonde hair to a platinum blonde level.

The term "undertone" as used herein refers to the typically unwanted natural color tone of hair after a lightning process. In blondes, this natural undertone is typically yellow to orange or brown.

The term "overtoning" as used herein refers to how much the hair has picked up from a treatment composition. In contrast, the term "neutralizing" means that the resultant hair tone after contact with the inventive composition results in the brassy undertone exposed during the bleaching process is neutralized and the hair appears as if it is a natural shade, and the term "toning" mean that the resultant hair tone after contact with the inventive composition results in the brassy undertone that is exposed during the bleaching process is toned to achieve a shade that is desired by the consumer though the resultant shade may not be a natural shade, per se. Generally, toning and neutralizing may sometimes be referred to interchangeably, meaning collectively that the use of the inventive hair refreshing composition provides tonal adjustment to address the undertone revealed by lightening.

The term "refreshing" as used herein refers to conferring excellent restorative properties that include moisturizing, detangling, shine, and smoothness to the hair while also providing toning or neutralizing of brassiness to enable the consumer to achieve the desired color and brightness.

Color Toning System

In accordance with the disclosure, various non-limiting embodiments of the hair refreshing composition include a color toning system which comprise at least one direct dye.

Direct Dyes

In accordance with the disclosure, various non-limiting embodiments of the hair refreshing composition include one or more direct dyes present in the color toning system.

Examples of direct dyes include azo direct dyes; (poly) methine dyes such as cyanins, hemicyanins and styryls; carbonyl dyes; azine dyes; nitro(hetero)aryl dyes; tri(hetero) arylmethane dyes; porphyrin dyes; phthalocyanin dyes, and natural direct dyes, alone or as mixtures. Direct dyes may be selected from cationic and anionic direct dyes.

Cationic direct dyes can include Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green, Basic Orange 31, 1, Basic Red 2, Basic Red 12 Basic Red 22, Basic Red 76 Basic Red 51, Basic Violet 1, Basic Violet 2, Basic Violet 3, Basic Violet 10, Basic Violet 14, Basic Yellow 57 and Basic Yellow 87.

Anionic direct dyes can include Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2 (Ext. Violet 2), D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium and/or potassium.

Nitro dyes can include HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Blue 15, HC Blue No. 17, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

In accordance with the various embodiments, as exemplified herein, at least one direct dye according to the invention is selected from violet dyes and is selected from the group consisting of Violet 1, Basic Violet 2, Basic Violet 3, Basic Violet 10, Basic Violet 14, Acid Violet 9, Acid Violet 43, Acid Violet 49, D&C Violet 2 (Ext. Violet 2), Disperse Violet 1, HC Violet BS, HC Violet No. 1, HC Violet No. 2, and combinations thereof. Violet dyes are selected in particular for use with blonde hair in particular for lightened or lifted blonde hair, although they may be selected for other hair colors and types.

In some specific embodiments, the at least one direct dye is D&C Violet 2 (Ext. Violet 2). Ext. (external) Violet 2, also known as CI 60730, is a synthetic colorant, sometimes referred to in general terms as an anthraquinone color, that is used as a color additive in the formulation of a wide variety of products. The Ext. in its name designates that it is used for external applications only. In some embodiments Ext. Violet 2 imparts color to cosmetics and personal care products, and is subject to certification by the Food and Drug Administration (FDA). Ext. Violet 2, either alone or in combination with other ingredients.

Generally, Color additives are classified as straight colors, lakes, and mixtures. Straight colors are color additives that have not been mixed or chemically reacted with any other substance. Ext. Violet 2 is a straight color. Ext. D&C Violet No. 2 synonyms include: CI 60730, 6-((4-HYDROXY-1-ANTHRAQUINONYL)AMINO)-MONOSODIUM SALT M-TOLUENESULFONIC ACID, BENZENESULFONIC ACID, 2[(9,10DIHYDRO4HYDROXY9, 10DIOXO1ANTHRACENYL) AMINO]5METHYL MONOSODIUM SALT, EXT. VIOLET 2, M-TOLUENESULFONIC ACID, 6-((4-HYDROXY-1-ANTHRAQUINONYL)AMINO)-MONOSODIUM SALT, MONOSODIUM SALT M-TOLUENESULFONIC ACID, 6-((4-HYDROXY-1-ANTHRAQUINONYL)AMINO)-, MURASAKI401, and SODIUM 4-[(9,10-DIHYDRO-4-HYDROXY-9,10-DIOXO-1-ANTHRYL)AMINO]TOLUENE-3-SULPHONATE.

The chemical formula is shown below:

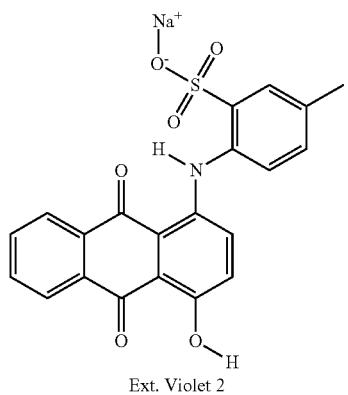

Ext. Violet 2

In some specific embodiments, the at least one direct dye excludes other dyes that are not violet dyes. In some specific embodiments, the at least one direct dye excludes other violet dyes except Ext. Violet 2. In some specific embodiments, the at least one direct dye excludes other violet dyes selected from the group consisting of HC VIOLET NO. 2, BASIC VIOLET 2, HC BLUE NO. 2, BASIC RED 51, and combinations thereof. In some specific embodiments, the at least one direct dye excludes each of HC VIOLET NO. 2, BASIC VIOLET 2, HC BLUE NO. 2, and BASIC RED 51.

In some particular embodiments, the violet toned direct dye consist of the direct dye EXT. VIOLET 2 present in the hair refreshing composition from about 0.5% to 1.0% by weight based on the total weight of the hair refreshing composition.

In some embodiments, the inventive compositions are provided with a concentration that can be selected from at least two different concentrations of the direct dye EXT. VIOLET 2 present in the hair refreshing composition from about 0.5% to 1.0%, wherein at one concentration, hair may be neutralized to accomplish a generally natural tone of the user, while at another concentration, hair may be toned to accomplish a violet hued tone that is generally not the natural tone of the user.

More generally, the total amount of direct dye in the hair refreshing composition may vary but is typically from about 0.0001% to 10% by weight and, for example, from 0.005% to 5% by weight based on the total weight of the composition. In some embodiments, the at least one direct dye is present from about 0.005% to 5% by weight based on the total weight of the composition. In some cases, the total amount of direct dye may be from about 0.001 to about 8 by weight based on the weight of the composition, about 0.001 to about 6 by weight based on the weight of the composition, about 0.001 to about 5 by weight based on the weight of the composition, about 0.001 to about 4 by weight based on the weight of the composition, about 0.001 to about 3 by weight based on the weight of the composition, about 0.01 to about 10 by weight based on the weight of the composition, about 0.01 to about 8 by weight based on the weight of the composition, about 0.01 to about 6 by weight based on the weight of the composition, about 0.01 to about 5 by weight based on the weight of the composition, about 0.01 to about 4 by weight based on the weight of the composition, about 0.01 to about 3 by weight based on the weight of the composition, about 0.1 to about 10 by weight based on the weight of the composition, about 0.1 to about 8 by weight based on the weight of the composition, about 0.1 to about 6 by weight based on the weight of the composition, or about 0.1 to about 5 by weight based on the weight of the composition, about 0.1 to about 4 by weight based on the weight of the composition, or about 0.1 to about 3 by weight based on the weight of the composition, based on the total weight of the composition.

Acidic Bonding Restorative Base

In accordance with the disclosure, various non-limiting embodiments of the hair refreshing composition include an acid bonding restorative base comprising at least one anionic surfactant comprising an isethionate surfactant, at least one ester comprising coco-caprylate/caprate; at least one cationic compound; at least one additional surfactant chosen from non-ionic and amphoteric surfactants; and water.

Anionic Surfactant

The acidic bonding restorative base comprises at least one first anionic surfactant chosen from isethionate surfactants. According to various embodiments, the at least one isethionate surfactant may be chosen from acyl isethionates of the following formulae (I) or (II):

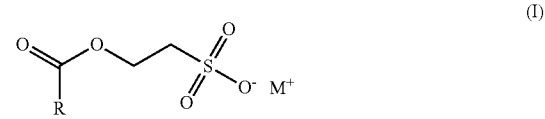

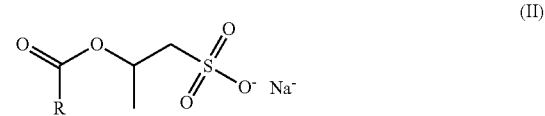

wherein R is chosen from H or an alkyl chain having from 1 to 30 carbon atoms, such as 6 to 24 carbon atoms, for example 8 to 20 carbon atoms, said chain being saturated or unsaturated, linear or branched, and $M^+$ is a cation. Although sodium is shown as the cation in formula (II), it should be understood that the cation for both formula (I) and formula (II) may be any alkali metal ion such as sodium or potassium, ammonium ions, or alkanolammonium ions such as monoethanolammonium or triethanolammonium ions.

By way of non-limiting example, suitable acyl isethionate surfactants may include the reaction product of fatty acids esterified with isethionic acid and neutralized with sodium hydroxide. For example, acyl isethionates surfactants may be prepared by the reaction of an isethionate salt such as metal or ammonium isethionate and an a saturated or unsaturated, straight or branched, alkyl or alkenyl chain fatty acid having from 6 to 30 carbon atoms, preferably from 8 to 22 carbon atoms, more preferably from 6 to 18 carbon atoms. Optionally, a mixture of aliphatic fatty acids may be used for the preparation of commercial fatty acyl isethionates surfactants. Suitable fatty acids for isethionate surfactants can be derived from coconut oil or palm kernel oil, for instance.

Non-limiting examples of acyl isethionate surfactants that may be used include sodium lauroyl isethionate, sodium lauroyl methyl isethionate, sodium oleoyl isethionate, sodium oleoyl methyl isethionate, sodium stearoyl isethionate, sodium stearoyl methyl isethionate, sodium myristoyl isethionate, sodium myristoyl methyl isethionate, sodium palmitoyl isethionate, sodium palmitoyl methyl isethionate, sodium cocoyl isethionate, sodium cocoyl methyl isethionate, a blend of stearic acid and sodium cocoyl isethionate, ammonium cocoyl isethionate, ammonium cocoyl methyl isethionate, and combinations thereof.

The total amount of isethionate surfactants may range up to about 15%, such as from about 4% to about 15% by weight, based on the total weight of the hair refreshing composition. For example, the total amount of isethionate surfactants may range from about 4% to about 14%, about 4% to about 13%, about 4% to about 12%, about 4% to about 11%, about 4% to about 10%, about 4% to about 9%, about 4% to about 8%, about 4% to about 7%, about 4% to about 6%, about 5% to about 15%, about 5% to about 14%, about 5% to about 13%, about 5% to about 12%, about 5% to about 11%, about 5% to about 10%, about 5% to about 9%, about 5% to about 8%, about 5% to about 7%, about 6% to about 15%, about 6% to about 14%, about 6% to about 13%, about 6% to about 12%, about 6% to about 11%, about 6% to about 10%, about 6% to about 9%, about 6% to about 8%, about 7% to about 15%, about 7% to about 14%, about 7% to about 13%, about 7% to about 12%, about 7% to about 11%, about 7% to about 10%, about 7% to about 9%, about 8% to about 15%, about 8% to about 14%, about 8% to about 13%, about 8% to about 12%, about 8% to about 11%, about 8% to about 10%, about 9% to about 15%, about 9% to about 14%, about 9% to about 13%, about 9% to about 12%, about 9% to about 11%, about 10% to about 15%, about 10% to about 14%, about 10% to about 13%, about 10% to about 12%, about 11% to about 15%, about 11% to about 14%, about 1% to about 13%, about 12% to about 15%, about 12% to about 14%, or about 13% to about 15% by weight, based on the total weight of the hair refreshing composition, including ranges and sub-ranges there between.

In various embodiments, the total amount of isethionate surfactants may range from about 90% to about 99.9%, by weight relative to the weight of the acidic bonding restorative base. For example, the total amount of isethionate surfactants may range from about 91% to about 99%, such as about 92% to about 98%, about 93% to about 97%, or about 94% to about 96%, including all ranges and sub-ranges there between, by weight relative to the weight of the acidic bonding restorative base. In various embodiments, the total amount of isethionate surfactants may be about 90%, about 91%, about 92%, about 93%, about 94%, about 95%, about 96%, about 97% about 98%, or about 99% by weight, based on the total weight of the acidic bonding restorative base.

Additional Anionic Surfactants

The hair refreshing composition may optionally comprise at least one or more additional anionic surfactants, in addition to the one or more isethionate(s) of the acidic bonding restorative base. The combination of the one or more isethionate(s) with the second anionic surfactant(s) makes up the anionic surfactant system. As used herein, the term "anionic surfactant" means a surfactant comprising, as ionic or ionizable groups, only anionic groups. These anionic groups are preferably chosen from the groups $CO_2H$, $CO_2^-$, $SO_3H$, $SO_3^-$, $OSO_3H$, $OSO_3^-$ $O_2PO_2H$, $O_2PO_2H$, and $O_2PO_2^{2-}$.

When present, the at least one second anionic surfactant may be chosen from either non-sulfate or sulfate-based anionic surfactants.

In one embodiment, the hair refreshing composition is free or essentially free of sulfate-based surfactants. If present, sulfate-based anionic surfactants may be chosen from, for example, alkyl sulfates, alkyl ether sulfates, alkylamido ether sulfates, alkylaryl polyether sulfates, monoglyceride sulfates, or combinations thereof. In various embodiments, the anionic surfactant may be chosen from $(C_6-C_{24})$alkyl sulfates, $(C_6-C_{24})$alkyl ether sulfates, which are optionally ethoxylated, comprising from 2 to 50 ethylene oxide units, and combinations thereof, in particular in the form of alkali metal salts or alkaline-earth metal salts, ammonium salts or amino alcohol salts. More preferentially, the anionic surfactant(s) are chosen from $(C_{10}-C_{20})$alkyl ether sulfates, and in particular sodium lauryl ether sulfate, optionally containing 2.2 mol of ethylene oxide. In other embodiments, sodium lauryl sulfate, sodium lauryl ether sulfate, ammonium lauryl sulfate, ammonium lauryl ether sulfate, sodium laureth sulfate, or combinations thereof may be chosen.

In various exemplary embodiments, the anionic surfactant system comprises at least one second anionic surfactant chosen from non-sulfate anionic surfactants, such as, for example, alkylsulfonates, alkylamide sulfonates, alkylarylsulfonates, alpha-olefin sulfonates, paraffin sulfonates, alkylsulfosuccinates, alkyl ether sulfosuccinates, alkylamide sulfosuccinates, alkyl sulfoacetates, acylsarcosinates, acylglutamates, alkylsulfosuccinamates, acylisethionates and N-acyltaurates, salts of alkyl monoesters and polyglycoside-polycarboxylic acids, acyllactylates, salts of D-galactoside uronic acids, salts of alkyl ether carboxylic acids, salts of alkyl aryl ether carboxylic acids, and salts of alkylamido ether carboxylic acids; or the non-salified forms of all of these compounds, the alkyl and acyl groups of all of these compounds containing from 6 to 24 carbon atoms and the aryl group denoting a phenyl group. Some of these compounds may be oxyethylenated and then preferably comprise from 1 to 50 ethylene oxide units.

Useful alkyl sulfonates include those of formula (VI):

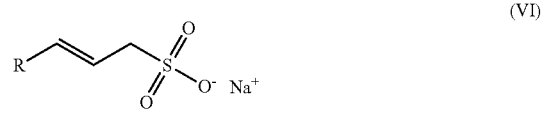

(VI)

wherein R is selected from H or alkyl chain that has from 1 to 30 carbon atoms, such as from 6 to 24 carbon atoms, for example from 8 to 20 carbon atoms, said chain being saturated or unsaturated, linear or branched. It should be noted that although sodium is shown as the cation in the above formula (VI), the cation may be any alkali metal ion such as sodium or potassium, ammonium ions, or alkanolammonium ions such as monoethanolammonium or triethanolammonium ions. In some instances, the alkyl sulfonate(s) are selected from C8-C16 alkyl benzene sulfonates, C10-C20 paraffin sulfonates, C10-C24 olefin sulfonates, salts thereof, and combinations thereof.

By way of non-limiting example, alkyl sulfonates may be chosen from alkyl aryl sulfonates, primary alkane disulfonates, alkene sulfonates, hydroxyalkane sulfonates, alkyl glyceryl ether sulfonates, alpha-olefinsulfonates, sulfonates of alkylphenolpolyglycol ethers, alkylbenzenesulfonates, phenvlalkanesulfonates, alpha-olefinsulfonates, olefin sulfonates, alkene sulfonates, hydroxyalkanesulfonates and disulfonates, secondary alkanesulfonates, paraffin sulfonates, ester sulfonates, sulfonated fatty acid glycerol esters, and alpha-sulfo fatty acid methyl esters including methyl ester sulfonate.

Non-limiting examples of useful alkyl sulfosuccinates include those of formula (VII):

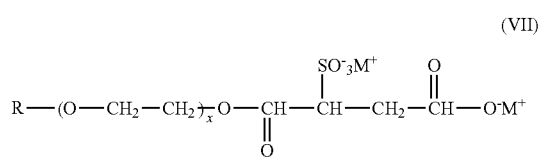

(VII)

wherein R is a straight or branched chain alkyl or alkenyl group having from 10 to 22 carbon atoms, such as 10 to 20 carbon atoms, and $M^+$ is a cation which can independently of each other be, for example, any alkali metal ion such as sodium, potassium, or ammonium, or alkanolammonium ions such as monoethanolammonium or triethanolammonium ions.

Non-limiting examples of alkyl sulfosuccinates salts include disodium oleamido MIPA sulfosuccinate, disodium oleamido MEA sulfosuccinate, disodium lauryl sulfosuccinate, disodium laureth sulfosuccinate, diammonium lauryl sulfosuccinate, diammonium laureth sulfosuccinate, dioctyl sodium sulfosuccinate, disodium oleamide MEA sulfosuccinate, sodium dialkyl sulfosuccinate, and a mixture thereof.

Exemplary and non-limiting alkyl sulfoacetates include C4-C18 fatty alcohol sulfoacetates and/or salts thereof, such as sodium lauryl sulfoacetate. Useful cations for the salts include any alkali metal ion such as sodium or potassium, ammonium ions, or alkanolammonium ions such as monoethanolammonium or triethanolammonium ions.

Non-limiting examples of alkoxylated monoacids include compounds corresponding to formula (VIII):

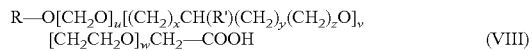

(VIII)

wherein:
R is a hydrocarbon radical containing from about 6 to about 40 carbon atoms;
u, v, and w, independently of one another, represent numbers of from 0 to 60;
x, y, and z, independently of one another, represent numbers of from 0 to 13;
R' represents hydrogen or alkyl; and
the sum of x+y+z>0.

Compounds corresponding to formula (VIII) may be obtained by alkoxylation of alcohols R—OH with ethylene oxide as the sole alkoxide, or with several alkoxides and subsequent oxidation. The numbers u, v, and w each represent the degree of alkoxylation. Whereas, on a molecular level, the numbers u, v, and w and the total degree of alkoxylation can only be integers, including zero, on a macroscopic level they are mean values in the form of broken numbers.

In formula (VIII), R is linear or branched, acyclic or cyclic, saturated or unsaturated, aliphatic or aromatic, substituted or unsubstituted. R may be a linear or branched, acyclic C6-40 alkyl or alkenyl group, or a C1-40 alkyl phenyl group, for example a C8-22 alkyl or alkenyl group or a C4-18 alkyl phenyl group, such as a C12-18 alkyl group or alkenyl group or a C6-16 alkyl phenyl group; u, v, w, independently of one another, may be a number from 2 to 20, for example a number from 3 to 17, such as a number from 5 to 15; x, y, z, independently of one another, may be a number from 2 to 13, for example a number from 1 to 10, such as a number from 0 to 8.

By way of example only, useful alkoxylated monoacids include Butoxynol-5 Carboxylic Acid, Butoxynol-19 Carboxylic Acid, Capryleth-4 Carboxylic Acid, Capryleth-6 Carboxylic Acid, Capryleth-9 Carboxylic Acid, Ceteareth-25 Carboxylic Acid, Coceth-7 Carboxylic Acid, C9-11 Pareth-6 Carboxylic Acid, C11-15 Pareth-7 Carboxylic Acid, C12-13 Pareth-5 Carboxylic Acid, C12-13 Pareth-8 Carboxylic Acid, C12-13 Pareth-12 Carboxylic Acid, C12-15 Pareth-7 Carboxylic Acid, C12-15 Pareth-8 Carboxylic Acid, C14-15 Pareth-8 Carboxylic Acid, Deceth-7 Carboxylic Acid, Laureth-3 Carboxylic Acid, Laureth-4 Carboxylic Acid, Laureth-5 Carboxylic Acid, Laureth-6 Carboxylic Acid, Laureth-8 Carboxylic Acid, Laureth-10 Carboxylic Acid, Laureth-11 Carboxylic Acid, Laureth-12 Carboxylic Acid, Laureth-13 Carboxylic Acid, Laureth-14 Carboxylic Acid, Laureth-17 Carboxylic Acid, PPG-6-Laureth-6 Carboxylic Acid, PPG-8-Steareth-7 Carboxylic Acid, Myreth-3 Carboxylic Acid, Myreth-5 Carboxylic Acid, Nonoxynol-5 Carboxylic Acid, Nonoxynol-8 Carboxylic Acid, Nonoxynol-10 Carboxylic Acid, Octeth-3 Carboxylic Acid, Octoxynol-20 Carboxylic Acid, Oleth-3 Carboxylic Acid, Oleth-6 Carboxylic Acid, Oleth-10 Carboxylic Acid, PPG-3-Deceth-2 Carboxylic Acid, Capryleth-2 Carboxylic Acid, Ceteth-13 Carboxylic Acid, Deceth-2 Carboxylic Acid, Hexeth-4 Carboxylic Acid, Isosteareth-6 Carboxylic Acid, Isosteareth-11 Carboxylic Acid, Trudeceth-3 Carboxylic Acid, Trideceth-6 Carboxylic Acid, Trideceth-8 Carboxylic Acid, Trideceth-12 Carboxylic Acid, Trideceth-3 Carboxylic Acid, Trideceth-4 Carboxylic Acid, Trideceth-7 Carboxylic Acid, Trideceth-15 Carboxylic Acid, Trideceth-19 Carboxylic Acid, Undeceth-5 Carboxylic Acid and combinations thereof. In some cases, preferred ethoxylated acids include Oleth-10 Carboxylic Acid, Laureth-5 Carboxylic Acid, Laureth-11 Carboxylic Acid, and combinations thereof.

Acyl amino acids that may be used include, but are not limited to, amino acid surfactants based on alanine, arginine, aspartic acid, glutamic acid, glycine, isoleucine, leucine, lysine, phenylalanine, serine, tyrosine, valine, sarcosine, threonine, and taurine. The most common cation associated with the acyl amino acid can be sodium or potassium. Alternatively, the cation can be an organic salt such as triethanolamine (TEA) or a metal salt. Non-limiting examples of useful acyl amino acids include those of formula (IX):

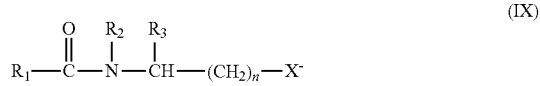

(IX)

wherein R, R1, R2, and R3 are each independently selected from H or an alkyl chain having from 1 to 30 carbon atoms, said chain being saturated or unsaturated, linear or branched, and X is $COO^-$ or $SO_3^-$.

By way of example, useful acyl amino acids include acyl taurates, acyl glycinates, acyl glutamates, acyl sarcosinates, salts thereof, and combinations thereof.

Exemplary useful acyl taurates include those of formula (X):

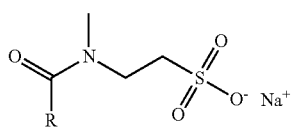
(X)

wherein R is selected from H or an alkyl chain having from 1 to 30 carbon atoms, such as from 6 to 24 carbon atoms, for example from 8 to 20 carbon atoms, said chain being saturated or unsaturated, linear or branched. It should be noted that although sodium is shown as the cation in the above formula (X), the cation may be any alkali metal ion such as sodium or potassium, ammonium ions, or alkanolammonium ions such as monoethanolammonium or triethanolammonium ions. Non-limiting examples of acyl taurate salts include sodium cocoyl taurate, sodium methyl cocoyl taurate, and combinations thereof.

Exemplary useful acyl glycinates include those of formula (XI):

(XI)

wherein R is an alkyl chain of 8 to 16 carbon atoms. It should be noted that although sodium is shown as the cation in the above formula (XI), the cation may be any alkali metal ion such as sodium, potassium, or ammonium ions, or alkanolammonium ions such as monoethanolammonium or triethanolammonium ions. Non-limiting examples of acyl glycinates include sodium cocoyl glycinate, sodium lauroyl glycinate, sodium myristoyl glycinate, potassium lauroyl glycinate, and potassium cocoyl glycinate, and combinations thereof.

Exemplary useful acyl glutamates include those of formula (XII):

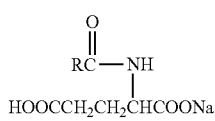
(XII)

wherein R is an alkyl chain of 8 to 16 carbon atoms. It should be noted that although sodium is shown as the cation in the above formula (XII), the cation may be any alkali metal ion such as sodium, potassium, or ammonium ions, or alkanolammonium ions such as monoethanolammonium or triethanolammonium ions. Non-limiting examples of acyl glutamates include dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, sodium undecylenoyl glutamate, triethanolamine mono-cocoyl glutamate, triethanolamine lauroylglutamate, disodium cocoyl glutamate, and combinations thereof.

Non-limiting examples of acyl sarcosinates include potassium lauroyl sarcosinate, potassium cocoyl sarcosinate, sodium cocoyl sarcosinate, sodium lauroyl sarcosinate, sodium myristoyl sarcosinate, sodium oleoyl sarcosinate, sodium palmitoyl sarcosinate, ammonium lauroyl sarcosinate, and combinations thereof.

When the anionic surfactant(s) are in salt form, they may be chosen especially from alkali metal salts such as the sodium or potassium salt and preferably the sodium salt, ammonium salts, amine salts and in particular amino alcohol salts, or alkaline-earth metal salts such as the magnesium salt. Examples of amino alcohol salts that may especially be mentioned include monoethanolamine, diethanolamine and triethanolamine salts, monoisopropanolamine, diisopropanolamine or triisopropanol-amine salts, 2-amino-2-methyl-1-propanol salts, 2-amino-2-methyl-1,3-propanediol salts and tris(hydroxymethyl)aminomethane salts. Alkali metal or alkaline-earth metal salts and in particular the sodium or magnesium salts may be used. Exemplary salts of $C_6$-$C_{24}$ alkyl monoesters of polyglycoside-polycarboxylic acids include $C_6$-$C_{24}$ alkyl polyglycoside-citrates, $C_6$-$C_{24}$ alkyl polyglycoside-tartrates and $C_6$-$C_{24}$ alkyl polyglycoside-sulfo succinates.

The anionic surfactant system may be present in the hair refreshing composition in an amount ranging from about 5% to about 25%, by weight, based on the total weight of the hair refreshing composition. For example, the anionic surfactant system may be present in an amount ranging from about 5% to about 24%, about 5% to about 23%, about 5% to about 22%, about 5% to about 21%, about 5% to about 20%, about 6% to about 25%, about 6% to about 24%, about 6% to about 23%, about 6% to about 22%, about 6% to about 21%, about 6% to about 20%, about 7% to about 25%, about 7% to about 24%, about 7% to about 23%, about 7% to about 22%, about 7% to about 21%, about 7% to about 20%, about 8% to about 25%, about 8% to about 24%, about 8% to about 23%, about 8% to about 22%, about 8% to about 21%, about 8% to about 20%, about 9% to about 25%, about 9% to about 24%, about 9% to about 23%, about 9% to about 22%, about 9% to about 21%, about 9% to about 20%, about 10% to about 25%, about 10% to about 24%, about 10% to about 23%, about 10% to about 22%, about 10% to about 21%, or about 10% to about 20%, including ranges and sub-ranges there between, by weight, based on the weight of the total composition.

The amount of the at least one second anionic surfactant, if present, will be chosen such that the total anionic surfactant system is present in the hair refreshing composition in the amounts described above, taking into consideration the amount of the first anionic surfactant chosen from isethionates.

Ester Comprising Coco-Caprylate Caprate

The acidic bonding restorative base also comprises coco-caprylate, coco-caprate, or coco-caprylate/caprate, which is a blend of coco-caprylate and coco-caprate (collectively referred to as "coco-caprylate/caprate"). Coco-caprylate/caprate is a straight, unbranched wax ester made of C12-C18 coconut fatty alcohol and a blend of fractionated fatty acids of vegetable origin. By way of non-limiting example, the coco-caprylate/caprate product DUB™ 810C from the company Stéarinerie Dubois may be used.

In various embodiments, the amount of coco-caprylate/caprate may range up to about 5% by weight, based on the total weight of the hair refreshing composition. For example, the coco-caprylate/caprate may be present in the hair refreshing composition in an amount ranging from about 0.001% to about 5%, about 0.01% to about 4%, about 0.05% to about 3%, about 0.01% to about 2%, about 0.5% to about 2%, about 0.1% to about 2%, about 0.01% to about 1%, about 0.05% to about 1%, about 0.1% to about 1%, about 0.01% to about 0.5%, about 0.05% to about 0.5%, or about 0.1% to about 0.5%, including ranges and sub-ranges there between, by weight, based on the total weight of the hair refreshing composition. In various exemplary embodiments, the amount of the coco-caprylate/caprate may be about 0.01%, about 0.02%, about 0.03%, about 0.04%, 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 3.0%, about 3.5%, about 4.0%, about 4.5%, or about 5.0%, by weight, based on the total weight of the hair refreshing composition.

In various embodiments, the total amount of coco-caprylate/caprate may range from about 0.5% to about 5%, by weight relative to the weight of the acidic bonding restorative base. For example, the total amount of coco-caprylate/caprate may range from about 1% to about 4%, such as about 1.5% to about 3.5%, about 1.75% to about 3.25%, or about 2% to about 3%, including all ranges and sub-ranges there between, by weight relative to the weight of the acidic bonding restorative base. In various embodiments the total amount of coco-caprylate/caprate may be about 0.5%, about 0.75%, about 1%, about 1.25%, about 1.5%, about 1.75%, about 2%, about 2.25%, about 2.5% about 2.75%, about 3%, about 3.25%, about 3.5%, about 3.75%, about 4%, about 4.25%, about 4.5%, about 4.75%, or about 5% by weight, based on the total weight of the acidic bonding restorative base.

Cationic Compound

The acidic bonding restorative base further comprises at least one cationic compound. Exemplary and non-limiting cationic compounds include cationic amine-based or quaternary ammonium-based compounds, cationic cellulose-based compounds, cationic starch-based compounds, cationic galactomannan compounds, and cationic silicone compounds.

In various exemplary embodiments, the at least one cationic compound may be chosen from cationic amine-based or quaternary ammonium-based compounds. By way of example, cationic amine-based compounds may be chosen from fatty amines, such as those comprising at least one C8-C30 hydrocarbon-based chain, for example a C12-C22 alkyl chain. As a non-limiting example, stearamidopropyl dimethylamine may be chosen.

Cationic quaternary ammonium-based compounds may be chosen from, for example, quaternary ammonium salts, such as compounds of formula (III):

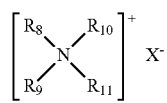

(III)

wherein:

(a) R8 to R11, which may be identical or different, represent a linear or branched aliphatic group comprising from 1 to 30 carbon atoms, or an aromatic group such as aryl or alkylaryl, it being understood that at least one of the groups R8 to R11 comprises from 12 to 22 carbon atoms, and preferably from 16 to 22 carbon atoms; and (b) X$^-$ represents an organic or mineral anionic counterion, such as that chosen from halides, acetates, phosphates, nitrates, (C1-C4)alkyl sulfates, (C1-C4)alkyl- or (C1-C4)alkylaryl sulfonates.

Non-limiting examples of cationic quaternary ammonium based compounds include tetraalkylammonium salts, for instance dialkyldimethylammonium or alkyltrimethylammonium salts in which the alkyl group contains approximately from 16 to 22 carbon atoms, in particular behenyltrimethylammonium, distearyldimethyl-ammonium, cetyltrimethylammonium or benzyldimethylstearylammonium salts, or, on the other hand, the palmitylamidopropyltrimethylammonium salt, the stearamido-propyltrimethylammonium salt, the stearamidopropyldimethylcetearylammonium salt, or the stearamidopropyldimethyl(myristyl acetate)ammonium salt, behentrimonium chloride, cetrimonium chloride, and behentrimonium methosulfate.

In further exemplary embodiments, the cationic compound may be a polysaccharide-based cationic compound, for example may be chosen from cationic cellulose derivatives such as those available from Amerchol Corp. (Edison, N.J., USA) in their Polymer JR™ and LR™ series of polymers, as salts of hydroxyethyl cellulose reacted with trimethyl ammonium substituted epoxide (referred to as Polyquaternium-10); polymeric quaternary ammonium salts of hydroxyethyl cellulose reacted with lauryl dimethyl ammonium-substituted epoxide (referred to as Polyquaternium-24), available from Amerchol Corp. under the tradename Polymer LM-200; or Polyquaternium-67 (quaternized hydroxyethyl cellulose), such as the product SOFTCAT® POLYMER SL 100 sold by the company Dow Chemical.

Other exemplary cationic Polyquaternium compounds useful according to the disclosure include, but are not limited to, Polyquaternium-1 (ethanol, 2,2',2"-nitrilotris-, polymer with 1,4-dichloro-2-butene and N,N,N',N'-tetramethyl-2-butene-1,4-diamine); Polyquaternium-2, (poly[bis(2-chloroethyl) ether-alt-1,3-bis[3-(dimethylamino)propyl]urea]); Polyquaternium-4, (hydroxyethyl cellulose dimethyl diallylammonium chloride copolymer; Diallyldimethylammonium chloride-hydroxyethyl cellulose copolymer); Polyquaternium-5 (copolymer of acrylamide and quaternized dimethylammoniumethyl methacrylate); Polyquaternium-6 (poly(diallyldimethyl-ammonium chloride)); Polyquaternium-7 (copolymer of acrylamide and diallyldimethylammonium chloride); Polyquaternium-8 (copolymer of methyl and stearyl dimethylaminoethyl ester of methacrylic acid, quaternized with dimethylsulphate); Polyquaternium-9 (homopolymer of N,N-(dimethylamino)ethyl ester of methacrylic acid, quaternized with bromomethane); Polyquaternium-11 (copolymer of vinylpyrrolidone and quaternized dimethylaminoethyl methacrylate); Polyquaternium-12 (ethyl methacrylate/abietyl methacrylate/diethylaminoethyl methacrylate copolymer quaternized with dimethyl sulfate); Polyquaternium-13 (ethyl methacrylate/oleyl methacrylate/diethylaminoethyl methacrylate copolymer quaternized with dimethyl sulfate); Polyquaternium-14 (trimethylaminoethylmethacrylate homopolymer); Polyquaternium-15 (acrylamide-dimethylaminoethyl methacrylate methyl chloride copolymer); Polyquaternium-16 (copolymer of vinylpyrrolidone and quaternized vinylimidazole); Polyquaternium-17 (adipic acid, dimethylaminopropylamine and dichloroethylether copolymer); Polyquaternium-18 (azelanic acid, dimethylaminopropylamine and dichloroethylether copolymer); Polyquaternium-19 (copolymer of polyvinyl alcohol and 2,3-epoxypropylamine); Polyquaternium-20 (copolymer of polyvinyl octadecyl ether and 2,3-epoxypropylamine); Polyquaternium-22 (copolymer of acrylic acid and diallyldimethylammonium chloride); Polyquaternium-27 (block copolymer of Polyquaternium-2 and Polyquaternium-17); Polyquaternium-28 (copolymer of vinylpyrrolidone and methacrylamidopropyl trimethylammonium); Polyquaternium-29 (chitosan modified with propylen oxide and quaternized with epichlorhydrin); Polyquaternium-30 (ethanaminium, N-(carboxymethyl)-N,N-dimethyl-2-[(2-methyl-1-oxo-2-propen-1-yl)oxy]-, inner salt, polymer with methyl 2-methyl-2-propenoate); Polyquaternium-31 (N,N-dimethylaminopropyl-N-acrylamidine quaternized with diethylsulfate bound to a block of polyacrylonitrile); Polyquaternium-32 (poly(acrylamide 2-methacryloxyethyltrimethyl ammonium chloride)); Polyquaternium-33 (copolymer of trimethylaminoethylacrylate salt and acrylamide); Polyquaternium-34 (copolymer of 1,3-dibromopropane and N,N-diethyl-N',N'-dimethyl-1,3-propanediamine); Polyquaternium-35 (methosulphate of the copolymer of methacryloyloxyethyltrimethylammonium and of methacryloyloxyethyldimethylacetyl-ammonium); Polyquaternium-36 (copolymer of N,N-dimethylaminoethylmethacrylate and butylmethacrylate, quaternized with dimethylsulphate); Polyquaternium-37 (poly(2-methacryloxyethyltrimethylammonium chloride)); Polyquaternium-39 (terpolymer of acrylic acid, acrylamide and diallyldimethylammonium Chloride); Polyquaternium-42 (poly[oxyethylene(dimethylimino)ethylene (dimethylimino)ethylene dichloride]); Polyquaternium-43 (copolymer of acrylamide, acrylamidopropyltrimonium chloride, 2-amidopropylacrylamide sulfonate and dimethylaminopropylamine); Polyquaternium-44 (3-Methyl-1-vinylimidazolium methyl sulfate-N-vinylpyrrolidone copolymer); Polyquaternium-45 (copolymer of (N-methyl-N-ethoxyglycine)methacrylate and N,N-dimethylaminoethylmethacrylate, quaternized with dimethyl sulphate); Polyquaternium-46 (terpolymer of vinylcaprolactam, vinylpyrrolidone, and quaternized vinylimidazole); Polyquaternium-47 (terpolymer of acrylic acid, methacrylamidopropyl trimethylammonium chloride, and methyl acrylate); and Polyquaternium-53 (terpolymer of acrylic acid/maptac/acrylamide).

In yet further exemplary embodiments, the cationic compound may be chosen from cationic galactomannan compounds, such as cationic guar-based compounds. For example, compounds such as guar gums containing trialkylammonium cationic groups may be chosen. Exemplary and non-limiting useful cationic guar gum compounds are those given the designation of guar hydroxypropyl trimonium chloride, available commercially for example as JAGUAR® C13S, which has a low degree of substitution of the cationic groups and a high viscosity. Other exemplary and non-limiting useful materials include that known as JAGUAR® C15, having a moderate degree of substitution and a low viscosity, JAGUAR® C17, and JAGUAR® C16 which is a hydroxypropylated cationic guar derivative containing a low level of substituent groups as well as cationic quaternary ammonium groups. Guar hydroxypropyl trimonium chloride may also be available commercially for example as N-HANCE CG13 from the company Ashland. Also useful is hydroxypropyl guar hydroxypropyltrimonium chloride, commercially available as JAGUAR® 162.

In yet further embodiments, cationic silicone compounds, for example amino silicones, may be chosen. As used herein, the term "amino silicone" means any polyaminosiloxane, e.g., any polysiloxane comprising at least one primary, secondary or tertiary amine function or a quaternary ammonium group. By way of example, compounds of formula (IV) may be chosen:

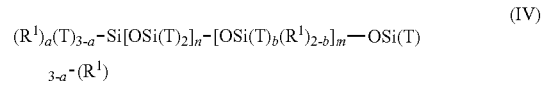

$$(R^1)_a(T)_{3-a} - Si[OSi(T)_2]_n - [OSi(T)_b(R^1)_{2-b}]_m - OSi(T)_{3-a} - (R^1) \qquad (IV)$$

wherein:
T is a hydrogen atom or a phenyl, hydroxyl (—OH) or C1-C8 alkyl radical, and preferably methyl, or a C1-C8 alkoxy, preferably methoxy;
a denotes the number 0 or an integer from 1 to 3, and preferably 0;
b denotes 0 or 1, preferably 1;
m and n are numbers such that the sum (n+m) can range especially from 1 to 2000 and in particular from 50 to 150, it being possible for n to denote a number from 0 to 1999 and in particular from 49 to 149, and for m to denote a number from 1 to 2000 and in particular from 1 to 10;
R1 is a monovalent radical of formula —CqH2qL in which q is a number from 2 to 8 and L is an optionally quaternized amino group selected from the following groups: N(R2)-CH2-CH2-N(R2)2; N(R2)2; N(R2)3Q-; N+(R2)(H)2Q-; N+(R2)2HQ-; N(R2)-CH2-CH2-N+(R2)(H)2Q-; and
R2 denotes a hydrogen atom, a phenyl, a benzyl or a saturated monovalent hydrocarbon-based radical, for example a C1-C20 alkyl radical; and
Q– represents a halide ion, for instance fluoride, chloride, bromide or iodide.

By way of example, trimethylsilylamodimethicone may be chosen.

In a further example, cationic amino silicones may be chosen from those of formula (V):

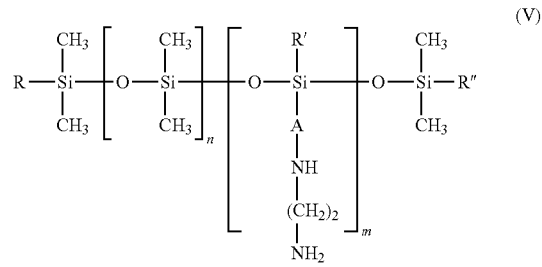

wherein:
R, R' and R", which may be identical or different, denote a C1-C4 alkyl radical, preferably CH3; a C1-C4 alkoxy radical, preferably methoxy; or —OH;
A represents a linear or branched, C3-C8 and preferably C3-C6 alkylene radical; and
m and n are integers dependent on the molecular weight and whose sum is between 1 and 2000.

In one embodiment, in formula (V), R, R', R", which may be identical or different, represent a C1-C4 alkyl or hydroxyl radical, A represents a C3 alkylene radical and m and n are such that the weight-average molecular weight of the compound is between about 5000 and 500,000. Compounds of this type are referred to as "aminodimethicones."

In a further embodiment, in formula (V), R, R' and R", which may be identical or different, represent a C1-C4 alkoxy or hydroxyl radical, at least one of the radicals R or R" is an alkoxy radical and A represents a C3 alkylene radical. The hydroxy/alkoxy molar ratio may be between 0.2/1 and 0.4/1, for example equal to 0.3/1. Moreover, m and n are such that the weight-average molecular weight of the compound is between about 2000 and $10^6$. More particularly, n is between 0 and 999 and m is between 1 and 1000, the sum of n and m being between 1 and 1000. For example, the product BELSIL® ADM 652 sold by Wacker may be chosen.

In yet a further embodiment, in formula (V) R and R", which are different, represent a C1-C4 alkoxy or hydroxyl radical, at least one of the radicals R or R" is an alkoxy radical, R' represents a methyl radical, and A represents a C3 alkylene radical. The hydroxy/alkoxy molar ratio is preferably between 1/0.8 and 1/1.1, for example equal to 1/0.95. Moreover, m and n are such that the weight-average molecular weight of the compound is between about 2000 and 200,000. More particularly, n is between 0 and 999 and m is between 1 and 1000, the sum of n and m being between 1 and 1000. For example, the product FLUID WR® 1300 sold by Wacker may be chosen.

In a still further embodiment, in formula (V) R and R" represent a hydroxyl radical, R' represents a methyl radical, and A is a C4-C8, preferably C4, alkylene radical. Moreover, m and n are such that the weight-average molecular weight of the compound is between about 2000 and $10^6$. More particularly, n is between 0 and 1999 and m is between 1 and 2000, the sum of n and m being between 1 and 2000. For example, the product DC 28299 by Dow Corning may be chosen.

The at least one cationic compound may be present in the hair refreshing composition in an amount ranging up to about 5% by weight, based on the total weight of the hair refreshing composition. For example, the at least one cationic compound may be present in the hair refreshing composition in an amount ranging from about 0.001% to about 5%, about 0.01% to about 4%, about 0.05% to about 3%, about 0.01% to about 2%, about 0.5% to about 2%, about 0.1% to about 2%, about 0.01% to about 1%, about 0.05% to about 1%, about 0.1% to about 1%, about 0.01% to about 0.5%, about 0.05% to about 0.5%, or about 0.1% to about 0.5%, including ranges and sub-ranges there between, by weight, based on the total weight of the hair refreshing composition. In various exemplary embodiments, the amount of the at least one cationic compound may be about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 3.0%, about 3.5%, about 4.0%, about 4.5%, or about 5.0%, by weight, based on the total weight of the hair refreshing composition.

In various embodiments, the total amount of the cationic compound may range from about 0.5% to about 5%, by weight relative to the weight of the acidic bonding restorative base. For example, the total amount of the polysaccharide-based cationic compound may range from about 1% to about 4%, such as about 1.5% to about 3.5%, about 1.75% to about 3.25%, about 1.75% to about 2.75%, or about 2% to about 3%, including all ranges and sub-ranges there between, by weight relative to the weight of the acidic bonding restorative base. In various embodiments the total amount of the cationic compound may be about 0.5%, about 0.75%, about 1%, about 1.25%, about 1.5%, about 1.75%, about 2%, about 2.25%, about 2.5% about 2.75%, about 3%, about 3.25%, about 3.5%, about 3.75%, about 4%, about 4.25%, about 4.5%, about 4.75%, or about 5% by weight, based on the total weight of the acidic bonding restorative base.

Additional Surfactants

Optionally, the hair refreshing composition may comprise other surfactants in addition to those of the anionic surfactant system. By way of example, the hair refreshing composition may comprise non-ionic and/or amphoteric surfactants.

As exemplary and non-limiting non-ionic surfactants, alkyl polyglucosides and/or monounsaturated glyceryl esters may be chosen.

In certain embodiments, the hair refreshing composition comprises at least one alkyl polyglucoside having the following formula (XIII):

$$R^1—O—(R^2O)_n—Z(x) \quad \text{(XIII)}$$

wherein:
$R^1$ is an alkyl group having from 8 to 18 carbon atoms;
$R^2$ is an ethylene or propylene group;
Z is a saccharide group with 5 to 6 carbon atoms;
n is an integer from 0 to 10; and
x is an integer from 1 to 5.

Nonlimiting examples of alkyl polyglucosides include lauryl glucoside, octyl glucoside, decyl glucoside, coco glucoside, caprylyl/capryl glucoside, and sodium lauryl glucose carboxylate. In certain embodiments, the at least one alkyl poly glucoside compound is selected from the group consisting of lauryl glucoside, decyl glucoside, coco glucoside, and combinations thereof.

The total amount of alkyl polyglucosides in the hair refreshing composition may vary, but typically ranges from about 0.01% to about 15%, such as about 0.1% to about 15%, or about 1% to about 15% by weight, based on the total weight of the hair refreshing composition. For example, the total amount of alkyl polyglucosides may range from about 5% to about 15%, from about 6% to about 14%, from about 7% to about 13%, from about 7% to about 12%, from about 8% to about 12%, from about 9% to about 12%, or from about 10% to about 12%, including ranges and sub-ranges there between, by weight based on the total weight of the hair refreshing composition. In various non-limiting embodiments, the total amount of alkyl polyglucosides is about 5%, about 6%, about 7%, about 8%, about 9%, about 10%, about 11%, about 12%, about 13%, about 14%, or about 15%, by weight based on the total weight of the hair refreshing composition.

In certain embodiments, the hair refreshing composition may comprise monounsaturated glyceryl esters such as, for example, glyceryl behenate, glyceryl caprate, glyceryl cocoate, glyceryl erucate, glyceryl hydroxystearate, glyceryl isostearate, glyceryl lanolate, glyceryl laurate, glyceryl linoleate, glyceryl myristate, glyceryl oleate, glyceryl palmitate lactate, glyceryl sesquioleate, glyceryl stearate, glyceryl stearate citrate, glyceryl stearate lactate, or combinations thereof. In certain embodiments, the at least one monounsaturated glyceryl ester may be chosen from polyglyceryl-4 isostearate, polyglyceryl-3 oleate, polyglyceryl-2 sesquioleate, triglyceryl diisostearate, diglyceryl monooleate, tetraglyceryl monooleate, or combinations thereof.

Optionally, the hair refreshing composition may further comprise at least one amphoteric surfactant. Non-limiting examples of amphoteric surfactants include betaines, sultaines, amphoacetates, amphoproprionates, and combinations thereof. In certain embodiments, betaines and amphoproprionates are used. In certain embodiments, betaines are used. Betaines which can be used in the current compositions include those having the following formulae (XIV)—(XVII):

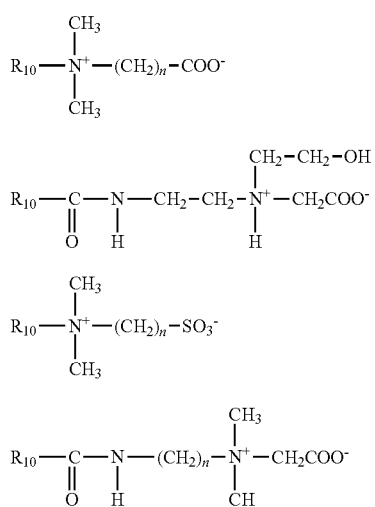

wherein in formulae (XIV)—(XVII):

R10 is an alkyl group having from 8 to 18 carbon atoms; and n is an integer from 1 to 3.

Non-limiting examples of betaines include coco betaine, cocoamidopropyl betaine, lauryl betaine, laurylhydroxy sulfobetaine, lauryldimethyl betaine, cocoamidopropyl hydroxysultaine, behenyl betaine, capryl/capramidopropyl betaine, lauryl hydroxysultaine, stearyl betaine, and combinations thereof. In certain embodiments, the at least one betaine compound may be chosen from the group consisting of coco betaine, cocoamidopropyl betaine, behenyl betaine, capryl/capramidopropyl betaine, lauryl betaine, and combinations thereof.

Hydroxyl sultaines useful in the hair refreshing composition according to embodiments of the disclosure include the following formula (XVIII):

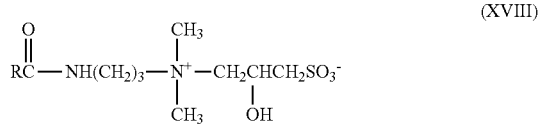

wherein R is an alkyl group having from 8 to 18 carbon atoms.

Useful alkylamphoacetates include those having the formula (XIX):

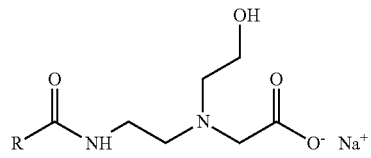

wherein R is an alkyl group having from 8 to 18 carbon atoms.

Useful alkyl amphodiacetates include those having the formula (XX):

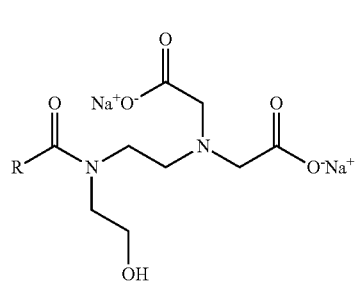

wherein R is an alkyl group having from 8 to 18 carbon atoms.

The amphoteric surfactants of the present disclosure may be optionally quaternized secondary or tertiary aliphatic amine derivatives, in which the aliphatic group is a linear or branched chain comprising from 8 to 22 carbon atoms, said amine derivatives containing at least one anionic group, for instance a carboxylate, sulfonate, sulfate, phosphate or phosphonate group.

Mention may be made in particular of ($C_8$-$C_{20}$)alkylbetaines, ($C_8$-$C_{20}$)alkylamido ($C_1$-$C_6$)alkylbetaines, sulfobetaines, ($C_8$-$C_{20}$)alkylsulfobetaines, ($C_8$-$C_{20}$)alkylamido ($C_1$-$C_6$)alkylsulfobetaines, ($C_8$-$C_{20}$)alkylamphoacetate, ($C_8$-$C_{20}$)alkylamphodiacetate, and combinations thereof.

Among the optionally quaternized secondary or tertiary aliphatic amine derivatives that may be used, mention may also be made of the products of respective structures (A1) and (A2) below:

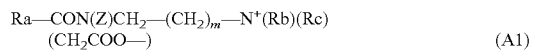

wherein:

Ra represents a $C_{10}$-$C_{30}$ alkyl or alkenyl group derived from an acid Ra—COOH preferably present in hydrolysed coconut oil, a heptyl group, a nonyl group or an undecyl group, Rb represents a μ-hydroxyethyl group, Rc represents a carboxymethyl group;

m is equal to 0, 1 or 2, and

Z represents a hydrogen atom or a hydroxyethyl or carboxymethyl group;

wherein:

B represents —CH$_2$CH$_2$OX', with X' representing —CH$_2$—COOH, CH$_2$—COOZ', CH$_2$CH$_2$—COOH, —CH$_2$CH$_2$—COOZ', or a hydrogen atom, B' represents —(CH$_2$)$_z$—Y', with z=1 or 2, and Y' representing COOH, COOZ', CH$_2$—CHOH—SO$_3$H or —CH$_2$—CHOH—SO$_3$Z', m' is equal to 0, 1 or 2, Z represents a hydrogen atom or a hydroxyethyl or carboxymethyl group, Z' represents an ion resulting from an alkali or alkaline-earth metal, such as sodium, potassium or magnesium; an ammonium ion; or an ion resulting from an organic amine and in particular from an amino alcohol, such as monoethanolamine, diethanolamine and triethanolamine, monoisopropanol-amine, diisopropanolamine or triisopropanolamine, 2-amino-2-methyl-1-propanol, 2-amino-2-methyl-1,3-propanediol and tris (hydroxymethyl)aminomethane, and Ra' represents a $C_{10}$-$C_{30}$ alkyl or alkenyl group of an acid Ra'COOH preferably pre-sent in hydrolysed linseed oil or coconut oil, an alkyl group, in particular a $C_{17}$ alkyl group, and its iso form, or an unsaturated $C_{17}$ group.

Exemplary amphoteric surfactants include sodium cocoamphoacetate, sodium lauroamphoacetate, sodium caproamphoacetate and sodium capryloamphoacetate. Further exemplary amphoteric surfactants include disodium cocoamphodiacetate, disodium lauroamphodiacetate, disodium caproamphodiacetate, disodium capryloamphodiacetate, disodium cocoamphodi-propionate, disodium lauroamphodipropionate, disodium caproamphodipropionate, disodium capryloamphodi-propionate, lauroamphodipropionic acid and coco-amphodipropionic acid.

Non-limiting examples that may be mentioned include the cocoamphodiacetate sold by the company Rhodia under the trade name Miranol® C2M Concentrate, the sodium cocoamphoacetate sold under the trade name Miranol Ultra C 32 and the product sold by the company Chimex under the trade name CHIMEXANE HA.

Use may also be made of the compounds of formula (XXI):

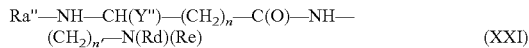

(XXI)

wherein:

Ra" represents a C10-C30 alkyl or alkenyl group of an acid Ra"—C(O)OH preferably present in hydrolysed linseed oil or coconut oil;

Y'" represents the group —C(O)OH, —C(O)OZ", —CH$_2$—CH(OH)—SO$_3$H or the group CH$_2$—CH (OH)—SO$_3$—Z", with Z" representing a cationic counterion resulting from an alkali metal or alkaline-earth metal, such as sodium, an ammonium ion or an ion resulting from an organic amine;

Rd and Re represent, independently of each other, a $C_1$-$C_4$ alkyl or hydroxyalkyl radical; and n and n' denote, independently of each other, an integer ranging from 1 to 3.

Exemplary compounds include sodium diethylaminopropylcoco-aspartamide, such as the one sold by the company Chimex under the name CHIMEXANE HB.

In certain embodiments, the amphoteric surfactants are chosen from ($C_8$-$C_{20}$)alkylbetaines, ($C_8$-$C_{20}$)alkylamido ($C_1$-$C_6$)alkylbetaines, ($C_5$-$C_{20}$)alkylamphoacetates and ($C_8$-$C_{20}$)alkylamphodiacetates, and combinations thereof.

In certain embodiments, the at least one amphoteric surfactant is chosen from ($C_8$-$C_{20}$)alkyl betaines, ($C_8$-$C_{20}$) alkylamido ($C_1$-$C_6$)alkylbetaines, ($C_8$-$C_{20}$)alkylamphoacetate, ($C_8$-$C_{20}$)alkylamphodiacetate, and their salts, and combinations thereof. In some cases, the at least one amphoteric surfactant is selected from coco-betaine, cocamidopropylbetaine, sodium cocoamphoacetate, disodium cocoamphodiacetate, and combinations thereof.

The amphoteric surfactant may be present in an amount up to about 10%, such as about 0.001% to about 10%, or about 0.001% to about 5% by weight, based on the total weight of the hair refreshing composition. For example, the amphoteric surfactant may be present in the hair refreshing composition in an amount ranging from about 0.001% to about 3%, about 0.01% to about 3%, about 0.05% to about 3%, about 0.1% to about 3%, about 1% to about 3%, about 1.5% to about 3%, about 2% to about 3%, about 2.5% to about 3%, about 0.01% to about 2%, about 0.05% to about 2%, about 0.1% to about 2%, about 0.01% to about 1%, about 0.05% to about 1%, about 0.1% to about 1%, or about 0.05% to about 0.5%, including ranges and sub-ranges there between, by weight, based on the total weight of the hair refreshing composition. In various exemplary embodiments, the amount of the amphoteric surfactant may be about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, or about 3.0% by weight, based on the total weight of the hair refreshing composition.

Emulsifiers

The hair refreshing composition according to the disclosure may optionally comprise one or more emulsifiers. In various embodiments, the emulsifiers may be chosen from fatty acids, fatty alcohols, esters of polyols and of a fatty acid, polyol fatty esters and fatty ethers with a branched or unsaturated chain containing from 10 to 30 carbon atoms, esters of sugar and of a fatty acid, and a mixture thereof. Nonlimiting examples of emulsifiers include ricinoleic acid, glycerol monostearate, glycol distearate, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, PEG-150 distearate, PEG-55 propylene glycol oleate, or combinations thereof.

In some particular embodiments, the hair refreshing composition may include one or more of glycol distearate, PEG-55 propylene glycol oleate, PEG-150 distearate and combinations thereof.

In some embodiments the hair refreshing composition may comprise two or more emulsifiers. The amount of each of the at least one emulsifier or a combination thereof, when present, may be present in the hair refreshing composition in a range of from about 0.001% to about 20%, or from about 0.01% to about 15%, or from about 0.1% to about 2%, or any suitable combination, sub-combination, range, or sub-range thereof by weight, based on the weight of the hair refreshing composition. One of ordinary skill in the art, however, will appreciate that other ranges are within the scope of the invention.

Thus, one or more emulsifier, when present, is present by weight, based on the total weight of the hair refreshing composition, from about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.5, 4.0, 4.5, 5.0, 6, 7, 8, 9, 10, 11, 12, 13, 14, 15, 16, 17, 18, 19 to about 20 percent, including increments and ranges therein and there between.

Cosmetically Acceptable Solvent

The hair refreshing composition according to the disclosure comprise water and at least one cosmetically acceptable solvent. In certain embodiments, the cosmetically acceptable solvents may be chosen from organic solvents, water-soluble solvents, water, or combinations thereof. In some embodiments, cosmetically acceptable solvents include glycerin, propylene glycol, and combinations thereof.

The total amount of cosmetically acceptable solvent with water in the hair refreshing composition may vary, but is typically from about 25% to about 95%, based on the total weight of the hair refreshing composition. In some cases, the total amount of water is about 30% to about 90%, about 35% to about 85%, about 40% to about 75%, about 45% to about 70%, or about 50% to about 67%, including ranges and sub-ranges there between, by weight based on the total weight of the hair refreshing composition.

Polymeric Thickener

In accordance with the disclosure, various non-limiting embodiments of the hair refreshing composition may optionally include one or more polymeric thickeners. In some embodiments, the one or more thickener may be selected from one or more of natural gums and synthetic polymers, for example, the thickener may be selected from the group consisting of starches (corn, rice, tapioca, potato), gums (xanthan carrageenan, gellan, *sclerotium*, tarabiotech fermentation). In some embodiments, the thickener may be selected from carbomer, acrylates/beheneth-25 methacrylate copolymer, acrylates/C10-30 alkyl acrylate crosspolymer, ammonium polyacryloyldimethyl taurate, ammonium acryloyldimethyltaurate/steareth-25 methacrylate crosspolymer, and polyacrylate crosspolymer-6, xanthan gum, hydroxypropyl guar, *Ceratonia siliqua* (carob) gum, and combinations thereof.

In some particular embodiments, the thickener may be selected from carbomer, acrylates/beheneth-25 methacrylate copolymer, and combinations thereof.

In some embodiments, the polymeric thickener may be one of carbomer, acrylates/beheneth-25 methacrylate copolymer, acrylates/C10-30 alkyl acrylate crosspolymer, polyacrylate crosspolymer-6, microcrystalline cellulose (and) cellulose gum, xanthan gum, sodium carboxymethyl starch, *Sclerotium* gum (and) xanthan gum, xanthan gum (and) *Ceratonia siliqua* (carob) gum (50/50), dehydroxanthan gum, hydroxypropyl starch phosphate, *Sclerotium* gum (and) xanthan gum (75/25), *Sclerotium* gum, xanthan gum (and) *Sclerotium* gum (and) Lecithin (and) pullulan, or combinations thereof.

In some embodiments the hair refreshing composition may comprise two or more polymeric thickeners. The amount of each of the at least one polymeric thickener, when present, may be present in the hair refreshing composition in a range of from about 0.001% to about 2%, or from about 0.005% to about 1.5%, or from about 0.0075% to about 0.2%, or any suitable combination, sub-combination, range, or sub-range thereof by weight, based on the weight of the hair refreshing composition. One of ordinary skill in the art, however, will appreciate that other ranges are within the scope of the invention.

In some embodiments, the total amount of polymeric thickener in the hair refreshing composition, when present, is present from about 0.001% to about 5%, or from about 0.007% to about 0.5%, or from about 0.1% to about 0.3%, or from about 0.21% to about 0.29%, or any suitable combination, sub-combination, range, or sub-range thereof by weight, based on the weight of the hair refreshing composition. One of ordinary skill in the art, however, will appreciate that other ranges are within the scope of the invention.

Thus, one or more polymeric thickener, when present, is present by weight, based on the total weight of the hair refreshing composition, from about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.5, 4.0, 4.5 to about 5.0 percent, including increments and ranges therein and there between.

Preservatives

In accordance with the disclosure, various non-limiting embodiments of the hair refreshing composition may optionally include one or more preservatives and/or antimicrobials. Any preservative commonly used in cosmetic formulations is an acceptable preservative for the hair refreshing composition herein, such as phenoxyethanol, salicylic acid, members from the paraben family such as the methyl, ethyl, propyl, butyl or isobutyl parabens, 4-hydroxy benzoic acid, benzoic acid, sorbic acid, dehydroacetic acid, triclosan, benzyl alcohol, chlorophenesin, or for example.

In some embodiments, the preservative may comprise salicylic acid, present from about 0.1% to about 0.5%

In some embodiments, the preservative may comprise one or more of preservatives selected from the group consisting of organic acids, parabens, formaldehyde donors, phenol derivatives, quaternary ammoniums, alcohols, isothiazolinones, and combinations thereof. Preservatives having antibacterial activity are optionally present in the hair refreshing composition of the present invention. Examples of organic acid preservatives include, but are not limited to, sodium benzoate, potassium sorbate, benzoic acid and dehydroacetic acid, sorbic acid, and combinations thereof. A preferred organic acid preservative system includes a mixture of sodium benzoate and potassium sorbate. Examples of paraben preservatives include, but are not limited to, alkyl para-hydroxybenzoates, wherein the alkyl radical has from 1, 2, 3, 4, 5 or 6 carbon atoms and for example, from 1 to 4 carbon atoms e.g., methyl para-hydroxybenzoate (methylparaben), ethyl para-hydroxybenzoate (ethylparaben), propyl para-hydroxybenzoate (propylparaben), butyl para-hydroxybenzoate (butylparaben) and isobutyl para-hydroxybenzoate (isobutylparaben). Examples of formaldehyde donor preservatives include, but are not limited to, 1,3-Dimethylol-5,5-dimethylhydantoin (DMDM hydantoin), imidazolidinyl urea, gluteraldehyde, and combinations thereof. Examples of quaternary ammonium preservatives include, but are not limited to, benzalkonium chloride, methene ammonium chloride, benzethonium chloride, and combinations thereof. Examples of alcohol preservatives include, but are not limited to, ethanol, benzyl alcohol, dichlorobenzyl alcohol, phenoxyethanol, and combinations thereof. Examples of isothiazolone preservatives include, but are not limited to, methylchloroisothiazolinone, methylisothiazolinone, and combinations thereof.

Other suitable preservatives include, but are not limited to, chloroacetamide, triclosan and iodopropynyl butylcarbamate, pyridine derivatives (e.g., pyrithione and zinc pyrithione), chlorphenesin, phenyl mercuric salts, phenoxyethanol, and other known preservative systems.

In some embodiments, the preservative includes one or more preservatives, the one or combination present at a concentration, by weight of about 0.001% to about 5%, or alternatively about 0.05% to about 2.5% or alternatively about 0.1% to about 2.0%, based upon weight of the hair refreshing composition.

Thus, any one of or a combination of preservatives, when present, may be present, by weight, based on the total weight of the hair refreshing composition, is from about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 1.0, 1.1, 1.2, 1.3, 1.4, 1.5, 1.6, 1.7, 1.8, 1.9, 2, 3, 4, to about 5 weight percent, including increments and ranges therein and there between.

Additional Components

In various embodiments, it may be advantageous to include additional components in the hair refreshing composition according to the disclosure. By way of non-limiting example, it may be advantageous to include at least one carboxylic acid, such as at least one organic compound that includes one, two, three, or more carboxylic acid functional groups (—COOH) and at least one carbon atom. Exemplary and non-limiting carboxylic acids may include oxalic acid, malonic acid, malic acid, glutaric acid, citraconic acid, citric acid, maleic acid, glycolic acid, succinic acid, adipic acid, tartaric acid, fumaric acid, sebacic acid, benzoic acid, and glyoxylic acid monohydrate, as well as combinations thereof.

If present, the at least one carboxylic acid may be present in an amount up to about 5% by weight, relative to the weight of the hair refreshing composition. For example, the at least one carboxylic acid may be present in the hair refreshing composition in an amount ranging from about 0.001% to about 5%, about 0.01% to about 4%, about 0.05% to about 3%, about 0.01% to about 2%, about 0.5% to about 2%, about 0.1% to about 2%, about 0.01% to about 1.5%, about 0.05% to about 1.5%, about 0.1% to about 1.5%, about 0.01% to about 1%, about 0.05% to about 1%, or about 0.1% to about 1%, including ranges and sub-ranges there between, by weight, based on the total weight of the hair refreshing composition. In various exemplary embodiments, the amount of the at least one carboxylic acid may be about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 3.0%, about 3.5%, about 4.0%, about 4.5%, or about 5.0%, by weight, based on the total weight of the hair refreshing composition.

In further embodiments, the hair refreshing composition may optionally comprise at least one ethanolamine compound. By way of example only, the hair refreshing composition may comprise monoethanolamine (MEA), diethanolamine (DEA), triethanolamine (TEA), or a mixture thereof. If present, the at least one ethanolamine may range up to about 2%, such as up to about 1.5%, up to about 1%, up to about 0.5%, or up to about 0.1% by weight, such as about 0.01%, based on the total weight of the hair refreshing composition. For example, the ethanolamine may be present in the hair refreshing composition in an amount ranging from about 0.001% to about 2%, about 0.01% to about 2%, about 0.05% to about 2%, about 0.1% to about 2%, about 0.001% to about 1%, about 0.01% to about 1%, about 0.05% to about 1%, about 0.1% to about 1%, about 0.001% to about 0.5%, about 0.01% to about 0.5%, about 0.05% to about 0.5%, or about 0.1% to about 0.5%, including ranges and sub-ranges there between, by weight, based on the total weight of the hair refreshing composition.

The hair refreshing composition in certain embodiments may also optionally comprise stabilizers, for example sodium chloride, magnesium dichloride or magnesium sulfate.

The hair refreshing composition according to the disclosure may also comprise further additives chosen from nacreous agents, dyes or pigments, fragrances, mineral, plant or synthetic oils, waxes, vitamins (e.g., panthenol, Vitamin E, biotin, etc.), proteins including ceramides, vitamins, UV-screening agents, free-radical scavengers, antidandruff agents, hair-loss counteractants, hair restorers, preserving agents, and combinations thereof. A person skilled in the art will take care to select the optional additives and the amount thereof such that they do not harm the properties of the hair refreshing composition of the present disclosure.

In various embodiments, the additives are generally present in an amount ranging up to about 40% by weight of active material based on the total weight of the hair refreshing composition, such as up to about 30%, up to about 20%, up to about 15%, up to about 10%, up to about 5%, such as from about 0.01% to about 20%.

In some embodiments, the hair refreshing composition are free or essentially free of silicones. For example, the hair refreshing composition may in some embodiments include less than about 3%, less than about 2%, less than about 1%, or less than about 0.5% of silicones. In other embodiments, the hair refreshing composition comprise silicones, for example in an amount of from about 0.1% up to about 1%, such as up to about 2%, up to about 3%, up to about 4%, or up to about 5%. Non-limiting examples of silicones include amine-functionalized silicones (e.g., amodimethicone), dimethicone, bis-aminopropyl dimethicone, trimethyl silylamodimethicone, etc.

In some embodiments, the hair refreshing composition is free or essentially free of imidazolium-based compounds, ammonium-based compounds, and combinations thereof. In some particular embodiments the hair refreshing composition is free or essentially free of tributylmethyl ammonium, butyl-3-methylimidazolium octyl sulfate, butyl-3-methylimidazolium acetate, ethyl-3-methylimidazolium ethylsulfate, 1,3-ethyl imidazolium acetate, and combinations thereof.

The hair refreshing composition according to the disclosure may be contained in a jar, a tube, a bottle optionally equipped with a pump, or any suitable package.

Methods Preparing and of Use

The inventive hair refreshing composition is prepared by mixing the ingredients wherein the direct dyes are introduced at the beginning of the batch together with water to ensure complete dye solubilization. After batch formation, viscosity was evaluated over time in accordance with industry standard stability protocols to determine shelf stability based on stability of viscosity. Viscosity was evaluated at the following timepoints: 1 week, 4 weeks and 8 weeks at 4° C., 25° C., 45° C. and the resultant viscosity of the inventive composition is characterized as follows: Viscosity Ford Cup in a range from 50-80, Viscosity rheomat at 25° C. in a range from 20-28, wherein the composition is deemed stable if the viscosity change is not more than 5%, or 10%, or 20%.

According to various embodiments, the hair refreshing composition may be useful in methods of treating and/or caring for the skin, hair, and/or scalp. By way of example, when the hair refreshing composition are shampoo compositions or conditioning shampoo compositions, the hair refreshing composition may be useful in methods of cleansing and/or conditioning the hair and/or scalp. When the hair refreshing composition are skin care or skin cleansing compositions, the hair refreshing composition may be useful in methods of cleansing and/or caring for the skin.

The hair refreshing composition according to the disclosure may be applied to the skin, hair, and/or scalp and subsequently rinsed off. For example, the skin, hair, and/or scalp may be washed or cleansed in a first step of applying the hair refreshing composition of the disclosure onto the skin, hair, and/or scalp, followed by an optional second repeat step of washing, each step including a leave-on time, for example up to 10 minutes, up to 5 minutes, up to 2 minutes, up to 1 minute, up to 30 seconds, up to 20 seconds, up to 10 seconds, up to 5 seconds, etc., and concluding by rinsing the hair with water. In some exemplary embodiments, the leave-on time for the hair refreshing composition is from about 2 to about 5 minutes and in some embodiments at least 5 minutes.

The methods of treating and/or caring for the skin, hair, and/or scalp according to the disclosure may, in various embodiments, impart moisture benefits to the skin, or conditioning and manageability benefits to the hair, and enhanced or improved tone with reduction of brassiness even after the hair refreshing composition is rinsed off. In addition, hair treated with the hair refreshing composition according to the disclosure may, in certain exemplary embodiments, have consumer desired toning and/or neutralizing of hair undertone, particularly in lightened or color lifted blonde hair, and greater ease of detangling, greater smoothness, discipline without a greasy coating or weighed-down feeling, moisturized feel, split-end seal, and/or reduced static, may be more sleek, and/or may have greater frizz control, relative to hair not having been treated with a composition according to the disclosure.

It should be understood that various features and/or characteristics of differing embodiments herein may be combined with one another. It is therefore to be understood that numerous modifications may be made to the illustrative embodiments and that other arrangements may be devised without departing from the scope of the disclosure. Other embodiments will be apparent to those skilled in the art from consideration of the disclosure and practice of the various exemplary embodiments disclosed herein.

As used herein, the terms "comprising," "having," and "including" are used in their open, non-limiting sense.

The terms "a," "an," and "the" are understood to encompass the plural as well as the singular. Thus, the term "a surfactant" includes both a single surfactant and a plurality of surfactants.

The expression "one or more" means "at least one" and thus includes individual components as well as mixtures/combinations.

Other than in the operating examples, or where otherwise indicated, all numbers expressing quantities of ingredients and/or reaction conditions are to be understood as being modified in all instances by the term "about," meaning within +/−5%, 4%, 3%, 2%, or 1% of the indicated number. Ranges can be expressed herein as from "about" one particular value, and/or to "about" another particular value. When such a range is expressed, examples include from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

All percentages, parts and ratios herein are relative to the amount of active agent, based upon the total weight of the hair refreshing composition of the present disclosure, unless otherwise indicated.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

As used herein, the terms "free" and "essentially free" and "exclude/excludes" are intended to denote that the component is absent entirely from the hair refreshing composition, or is present in an amount considered by those skilled in the art to not provide an effect on the hair refreshing composition. For example, the component may be present in an amount below the level of detection, or may be present in an amount less than 3%, less than 2%, less than 1%, less than 0.5%, less than 0.1%, less than 0.01%, or less than 0.001%.

It should also be understood that the precise numerical values used in the specification and claims form additional embodiments of the disclosure, and are intended to include any ranges which may be narrowed to any two end points disclosed within the exemplary ranges and values provided, as well as the specific end points themselves. Efforts have been made to ensure the accuracy of the numerical values disclosed herein. Any measured numerical value, however, can inherently contain certain errors resulting from the standard deviation found in its respective measuring technique.

The hair refreshing composition and methods of the present disclosure can comprise, consist of, or consist essentially of the essential elements and limitations of the disclosure described herein, as well as any additional or optional ingredients, components, or limitations described herein or otherwise useful.

Unless otherwise expressly stated, it is in no way intended that any method set forth herein be construed as requiring that its steps be performed in a specific order. Accordingly, where a method claim does not expressly recite that a particular order of steps must be followed or it is not otherwise specifically stated in the claims or descriptions that the steps are to be limited to a specific order, it is no way intended that any particular order be inferred.

All patents and publications are expressly incorporated herein in their entireties.

EXAMPLES

The following examples serve to illustrate the embodiments of the disclosure without however exhibiting a limiting character. The Examples are intended to be non-restrictive and explanatory only, with the scope of the invention being defined by the claims. In these examples the amounts of the hair refreshing composition ingredients are given as weight percentages of active ingredients based on the total weight of the hair refreshing composition.

Example 1—Bonding Rinse-Off BASE

A bonding rinse-off BASE formulation is exemplified according to the list of ingredients shown in Table 1 for formulations A, B and C (e.g., shampoo form). Generally, the base formulation includes a combination of an isethionate surfactant (e.g., one or more of sodium cocoyl isethionate, sodium lauroyl methyl isethionate), Coco-Caprylate/Caprate, a cationic compound (e.g., POLYQUATERNIUM 10 and/or 67, or cationic guar), optionally one or more nonionic and/or amphoteric surfactants (e.g., one or more of glyceryl oleate, PEG-150 distearate, decyl glucoside, Coco-glucoside, coco-betaine; cocoamidopropyl betaine), and a combination of thickeners (e.g., one or more of carbomer and methacrylate polymer) and one or more additional ingredients (e.g., pH adjuster, chelating agent, alcohol, anti-microbial/preservative, vitamins, fragrance, etc.). The exemplified base compositions are more fully described in US. Patent Publication No. US20210267868A1.

TABLE 1

BONDING BASE FORMULATION

| US INCI NAME | FORMULATION A | FORMULATION B | FORMULATION C |
|---|---|---|---|
| GLYCOL DISTEARATE | 0.105 | 0.12 | 0.12 |
| COCO-GLUCOSIDE | 11.44 | — | 11.66 |
| SODIUM COCOYL ISETHIONATE | 11 | 11 | 11.00 |
| COCAMIDOPROPYL BETAINE | 2.584 | 2.584 | 2.584 |
| COCO-BETAINE | 0.021 | 0.024 | 0.099 |
| POLYQUATERNIUM-10 | 0.11 | — | — |
| POLYQUATERNIUM-67 | 0.2 | 0.2 | 0.20 |
| SODIUM CHLORIDE | 0.68055 | 0.4812 | 0.5 |
| PEG-55 PROPYLENE GLYCOL OLEATE | 0.4 | 0.4 | 0.40 |
| PEG-150 DISTEARATE | 1 | 0.5 | 0.5 |
| COCO-CAPRYLATE/CAPRATE | 0.38 | 0.2 | 0.20 |
| TRIDECETH-6 and/or PPG-5-CETETH 20 | — | 0.215 | 0.515 |
| CETRIMONIUM CHLORIDE | — | 0.003 | 0.03 |
| DECYL GLUCOSIDE | — | 11.66 | — |
| GLYCERIN/PROPYLENE GLYCOL | — | 0.75 | 1.15 |
| DIMETHICONE | — | 0.75 | 0.75 |
| AMODIMETHICONE | — | 0.171 | 0.17 |
| CARBOMER and/or ACRYLATES/BEHENETH-25 METHACRYLATE COPOLYMER | — | 0.271 | 0.365 |
| ADDITIONAL COMPONENTS (one or more of: alcohol, citric acid, fragrance, panthenol, salicylic acid, sodium benzoate, sodium hydroxide, sodium phytate) | 1.610 | 2.910 | 3.6 |
| WATER | QS (~67) | QS (~67) | QS (~67) |
| pH | 6.0 | 5.7 | |

In some embodiments, base formulations, for example Formulation C, may include the following ingredients in quantities in amounts by total weight of the composition that include: trideceth-6 and PPG-5-CETETH 20, present respectively at about 0.015 and 0.5 by weight based on the weight of the composition; glycerin and propylene glycol, present respectively at about 0.75 and 0.4 by weight based on the weight of the composition; carbomer and/or acrylates/beheneth-25 methacrylate copolymer present respectively at about 0.29 and 0.75 by weight based on the weight of the composition; and alcohol, citric acid, fragrance, panthenol, salicylic acid, sodium benzoate, sodium hydroxide, and sodium phytate present in a range from about 0.003 to about 1.0 by weight based on the weight of the composition.

The base formulations provide a surprisingly dense, lush, creamy foam, with a viscosity that would be typical of a shampoo composition despite the inclusion of esters that would be expected to negatively affect the aesthetic cosmetic properties of a shampoo.

When applied to wet hair, then lathered, rinsed, combed, dried, and styled, the formulations lather very well, coat the hair nicely, rinse easily from the hair, and confer ease of detangling the wet hair is superior. After the hair is dried and styled, the hair has excellent properties of shine and frizz control, is moisturized but not greasy, demonstrates good manageability, shaping, and discipline (e.g., no "fly-aways"), and has smooth ends.

Employing certain general features of the exemplified base formulation, the inventive composition according to the instant disclosure was developed to confer in a single step process both bonding and color refreshing.

Example 2—Inventive Composition

The inventive composition includes an acidic bonding restorative base generally as set forth in Example 1, together with the color toning system useful for application to lightened blonde hair wherein the direct dye is a violet dye comprising EXT. Violet 2.

TABLE 2

INVENTIVE COMPOSITION

| US INCI NAME | INVENTIVE 1 | INVENTIVE 2 |
|---|---|---|
| GLYCOL DISTEARATE | 0.12 | 0.12 |
| SODIUM COCOYL ISETHIONATE | 11.0 | 11.0 |
| COCAMIDOPROPYL BETAINE | 2.584 | 2.584 |
| COCO-BETAINE | 0.099 | 0.099 |
| POLYQUATERNIUM-67 | 0.200 | 0.200 |
| SODIUM CHLORIDE | 0.5 | 0.5 |
| PEG-55 PROPYLENE GLYCOL OLEATE | 0.4 | 0.4 |
| PEG-150 DISTEARATE | 0.5 | 0.5 |
| COCO-CAPRYLATE/CAPRATE | 0.2 | 0.2 |
| TRIDECETH-6 and/or PPG-5-CETETH 20 | 0.515 | 0.515 |

TABLE 2-continued

| | INVENTIVE COMPOSITION | |
|---|---|---|
| US INCI NAME | INVENTIVE 1 | INVENTIVE 2 |
| CETRIMONIUM CHLORIDE | 0.003 | 0.003 |
| DECYL GLUCOSIDE | 11.66 | 11.66 |
| GLYCERIN/PROPYLENE GLYCOL | 1.15 | 1.15 |
| DIMETHICONE | 0.75 | 0.75 |
| AMODIMETHICONE | 0.17 | 0.17 |
| CARBOMER and/or ACRYLATES/BEHENETH-25 METHACRYLATE COPOLYMER | 0.369 | 0.369 |
| EXT. VIOLET 2 | 0.5 | 0.3 |
| ADDITIONAL COMPONENTS (alcohol, citric acid, fragrance, panthenol, salicylic acid, sodium benzoate, sodium hydroxide, sodium phytate) | 4.15 | 4.15 |
| WATER | QS (~66) | QS (~66) |
| pH | 5.53 | 5.50 |
| Properties | Optimal Toning; demonstrated stability at the time of formulation and over time up to at least 8 weeks | Moderate Toning; demonstrated stability at the time of formulation and over time up to at least 8 weeks |

In some embodiments, inventive compositions may include the following ingredients in quantities in amounts by total weight of the composition that include: trideceth-6 and PPG-5-CETETH 20, present respectively at about 0.015 and 0.5 by weight based on the weight of the composition; glycerin and propylene glycol, present respectively at about 0.75 and 0.4 by weight based on the weight of the composition; carbomer and/or acrylates/beheneth-25 methacrylate copolymer present respectively at about 0.29 and 0.75 by weight based on the weight of the composition; alcohol, citric acid, fragrance, panthenol, salicylic acid, sodium benzoate, sodium hydroxide, and sodium phytate present in a range from about 0.003 to about 1.0 by weight based on the weight of the composition, for example, respectively, 0.003, 1.0, 0.8, 1.0, 0.2, 0.5, 0.5, and 0.15 by weight based on the weight of the composition.

Referring to FIG. 1, a photographic image shows hair swatches treated with control (no treatment), comparative and inventive compositions according to the disclosure. Thus, FIG. 1 affords an example demonstrating toning efficacy of the above inventive composition formulations as applied to and subsequently rinsed from hair swatch samples that were earlier subject to lighting to level 7 lifting. As shown, the two test swatches to which respective embodiments of the inventive composition was applied demonstrate desirable neutralization and toning wherein. Additional observations of the formulations demonstrated physical stability and chemical stability based on satisfactory retention of the bulk tone.

Example 3—Comparative Compositions

The comparative compositions include an acidic bonding restorative base generally as set forth in Example 1, together with a color toning system that includes one or more direct dyes including violet, red and blue direct dyes to provide an overall violet bulk tone.

TABLE 2

| | COMPARATIVE COMPOSITIONS | | |
|---|---|---|---|
| US INCI NAME | COMPARATIVE 1 | COMPARATIVE 2 | COMPARATIVE 3 |
| GLYCOL DISTEARATE | 0.12 | 0.12 | 0.12 |
| SODIUM COCOYL ISETHIONATE | 11.0 | 11.0 | 11.0 |
| COCAMIDOPROPYL BETAINE | 2.584 | 2.584 | 2.584 |
| COCO-BETAINE | 0.099 | 0.099 | 0.099 |
| POLYQUATERNIUM-67 | 0.200 | 0.2 | 0.2 |
| SODIUM CHLORIDE | 0.5 | 0.5 | 0.5 |
| PEG-55 PROPYLENE GLYCOL OLEATE | 0.4 | 0.4 | 0.4 |
| PEG-150 DISTEARATE | 0.5 | 0.5 | 0.5 |
| COCO-CAPRYLATE/CAPRATE | 0.2 | 0.2 | 0.2 |
| TRIDECETH-6 and/or PPG-5-CETETH 20 | 0.515 | 0.515 | 0.515 |
| CETRIMONIUM CHLORIDE | 0.003 | 0.003 | 0.003 |
| DECYL GLUCOSIDE | 11.66 | 11.66 | 11.66 |
| GLYCERIN/PROPYLENE GLYCOL | 1.15 | 1.15 | 1.15 |
| DIMETHICONE | 0.75 | 0.75 | 0.75 |
| AMODIMETHICONE | 0.17 | 0.17 | 0.17 |
| CARBOMER and/or ACRYLATES/BEHENETH-25 METHACRYLATE COPOLYMER | 0.369 | 0.369 | 0.369 |
| HC VIOLET NO. 2 | 0.1 | | |
| BASIC VIOLET 2 | | 0.30 | |
| HC BLUE NO. 2 | | | 0.30 |
| BASIC RED 51 | 0.0008 | | |
| ADDITIONAL COMPONENTS (alcohol, citric acid, fragrance, | 3.95 | | |

TABLE 2-continued

COMPARATIVE COMPOSITIONS

| US INCI NAME | COMPARATIVE 1 | COMPARATIVE 2 | COMPARATIVE 3 |
|---|---|---|---|
| panthenol, salicylic acid, sodium benzoate, sodium hydroxide, sodium phytate) | | | |
| WATER | QS (~67) | QS (~67) | QS (~67) |
| pH | 5.58 | 5.55 | 5.49 |
| Properties | Insufficient toning at 5 min; shift in bulk tone over time | Overtoning at 5 min; insufficient neutralizing of brassiness; viscosity crashed over time | Overtoning at 5 min; viscosity crashed over time |

Comparative compositions include the following ingredients in quantities in amounts by total weight of the composition that include: trideceth-6 and PPG-5-CETETH 20, present respectively at about 0.015 and 0.5 by weight based on the weight of the composition; glycerin and propylene glycol, present respectively at about 0.75 and 0.4 by weight based on the weight of the composition; carbomer and/or acrylates/beheneth-25 methacrylate copolymer present respectively at about 0.29 and 0.75 by weight based on the weight of the composition; alcohol, citric acid, fragrance, panthenol, salicylic acid, sodium benzoate, sodium hydroxide, and sodium phytate present in a range from about 0.0003 to about 1.0 by weight based on the weight of the composition.

Referring again to FIG. 1, the photographic image affords an example demonstrating the toning efficacy of the above comparative composition formulations as applied to and subsequently rinsed from hair swatch samples that were earlier subject to lighting to level 7 lifting. Based on the demonstrated and above listed observations, the comparative formulations are inferior to the inventive hair refreshing composition because when tested they demonstrate one or more of the following failures: chemical instability as evidenced by insufficient tone neutralization of brassiness when applied to blonde hair indicating that the efficacy of the color toning system is diminished wherein the exemplified comparative compositions 2 and 3 demonstrated overtoning after 5 minutes which means that the hair took up too much of the direct dye colorant to be acceptable for a consumer; chemical instability as evidenced by change in bulk tone over time indicating a change in the chemistry of the color toning system; physical instability as evidenced by a drop in viscosity or a "break" in the formulation structure; and combinations of these.

The invention claimed is:

1. A hair refreshing composition comprising a color toning system comprising at least one direct dye that comprises EXT. VIOLET 2, and an acidic bonding restorative base, wherein;
   the acidic bonding restorative base comprises:
      at least one anionic surfactant comprising an isethionate surfactant;
      at least one ester comprising coco-caprylate/caprate;
      at least one cationic compound;
      at least one additional surfactant selected from the group consisting of non-ionic surfactants, amphoteric surfactants and combinations thereof; and
      water;
   the hair refreshing composition excludes HC VIOLET NO. 2, BASIC VIOLET 2, HC BLUE NO. 2, and BASIC RED 51;
   EXT. VIOLET 2 is present in the hair refreshing composition from about 0.1% to about 2% by weight based on the total weight of the hair refreshing composition; and
   the hair refreshing composition has a pH in a range from about pH 5.3 to about pH 5.9.

2. The hair refreshing composition according to claim 1, wherein the at least one direct dye is present in the hair refreshing composition from about 0.1% to 1.0% by weight based on the total weight of the hair refreshing composition.

3. The hair refreshing composition according to claim 1, wherein EXT. VIOLET 2 is present in the hair refreshing composition from about 0.5% to about 1.0% by weight based on the total weight of the hair refreshing composition.

4. The hair refreshing composition according to claim 1, wherein the at least one additional surfactant that comprises at least one non-ionic or amphoteric surfactant is selected from the group consisting of alkyl polyglucosides, monounsaturated glyceryl esters, betaines, sultaines, amphoacetates, amphopropionates, and combinations thereof.

5. The hair refreshing composition according to claim 1, wherein the at least one additional surfactant that comprises at least one non-ionic or amphoteric surfactant comprises at least one non-ionic surfactant comprising (i) one or more alkyl polyglucosides selected from the group consisting of lauryl glucoside, octyl glucoside, decyl glucoside, coco glucoside, caprylyl/capryl glucoside, and sodium lauryl glucose carboxylate, or combinations thereof, (ii) or one or more monounsaturated glyceryl esters selected from the group consisting of glyceryl behenate, glyceryl caprate, glyceryl cocoate, glyceryl erucate, glyceryl hydroxystearate, glyceryl isostearate, glyceryl lanolate, glyceryl laurate, glyceryl linoleate, glyceryl myristate, glyceryl oleate, glyceryl palmitate lactate, glyceryl sesquioleate, glyceryl stearate, glyceryl stearate citrate, glyceryl stearate lactate, polyglyceryl-4 isostearate, polyglyceryl-3 oleate, polyglyceryl-2 sesquioleate, triglyceryl diisostearate, diglyceryl monooleate, tetraglyceryl monooleate, or combinations thereof.

6. The hair refreshing composition according to claim 1, wherein the at least one additional surfactant that comprises at least one non-ionic or amphoteric surfactant comprises at least one amphoteric surfactant selected from the group consisting of coco betaine, cocoamidopropyl betaine, lauryl betaine, laurylhydroxy sulfobetaine, lauryldimethyl betaine, cocoamidopropyl hydroxysultaine, behenyl betaine, capryl/capramidopropyl betaine, lauryl hydroxysultaine, stearyl betaine, and combinations thereof.

7. The hair refreshing composition according to claim 1, wherein the at least one cationic compound is selected from the group consisting of cationic amine-based compounds, quaternary ammonium-based compounds, cationic cellulose-based compounds, cationic starch-based compounds, cationic galactomannan compounds, cationic silicone compounds, and combinations thereof.

8. The hair refreshing composition according to claim 1, wherein the at least one cationic compound is selected from the group consisting of cationic guar, Polyquaternium-10, Polyquaternium-67, and combinations thereof.

9. The hair refreshing composition according to claim 1, wherein the composition comprises at least one emulsifier selected from the group consisting of ricinoleic acid, glycerol monostearate, glycol distearate, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, PEG-150 distearate, PEG-55 propylene glycol oleate, and combinations thereof.

10. The hair refreshing composition according to claim 1, wherein the composition comprises at least one polymeric thickener selected from the group consisting of carbomer, acrylates/beheneth-25 methacrylate copolymer, acrylates/C10-30 alkyl acrylate crosspolymer, ammonium polyacryloyldimethyl taurate, ammonium acryloyldimethyltaurate/steareth-25 methacrylate crosspolymer, and polyacrylate crosspolymer-6, xanthan gum, hydroxypropyl guar, *Ceratonia siliqua* (carob) gum, and combinations thereof.

11. The hair refreshing composition according to claim 1, wherein the composition comprises at least one additional compound selected from the group consisting of pH adjuster, chelating agent, alcohol, antimicrobial, preservative, vitamin, fragrance, humectant, emulsifiers, and combinations thereof.

12. The hair refreshing composition according to claim 1, wherein the hair refreshing composition is free or essentially free of imidazolium-based compounds, ammonium-based compounds, and combinations thereof.

13. A hair refreshing composition comprising a color toning system, the color toning system comprising at least one violet toned direct dye, and an acidic bonding restorative base,
wherein the at least one violet toned direct dye comprises EXT. VIOLET 2 which is present from about 0.1% to about 2% by weight based on the total weight of the hair refreshing composition,
wherein the acidic bonding restorative base comprises:
  (a) at least one anionic surfactant selected from the group consisting of sodium cocoyl isethionate, sodium lauroyl isethionate, and combinations thereof present from about 4% to about 15% by weight, based on the total weight of the hair refreshing composition;
  (b) at least one ester comprising coco-caprylate/caprate present from about 0.01% to about 5% by weight, based on the total weight of the hair refreshing composition;
  (c) at least one cationic compound selected from the group consisting of polysaccharide-based cationic compounds, cationic silicone compounds, and combinations thereof;
  (d) at least one additional surfactant chosen from non-ionic and amphoteric surfactants and comprising:
    (i) at least one non-ionic surfactant comprising at least one alky polyglucoside present from about 7% to about 15% by weight, based on the total weight of the hair refreshing composition; and
    (ii) at least one amphoteric surfactant present from about 0.01% to about 7% by weight, based on the total weight of the hair refreshing composition;
  (e) at least one emulsifier; and
  (f) at least one cosmetically acceptable solvent comprising water,
wherein the hair refreshing composition has a pH in a range from about pH 5.3 to about pH 5.9, and
wherein the hair refreshing composition excludes HC VIOLET NO. 2, BASIC VIOLET 2, HC BLUE NO. 2, and BASIC RED 51.

14. A method for refreshing hair, comprising: contacting hair with a composition according to claim 1, wherein the hair is blonde hair that has been pre-lightened to a lifting level of up to 7.

15. The method for refreshing hair according to claim 14, wherein the violet toned direct dye comprising EXT. VIOLET 2 is present in the hair refreshing composition from about 0.1% to about 1% by weight based on the weight of the composition.

16. A process for altering the appearance of hair, the process comprising:
  a. providing a composition according to claim 1;
  b. contacting hair with the composition in (a) to form treated hair; and
  c. rinsing the treated hair,
  wherein the at least one violet toned direct dye comprising EXT. VIOLET 2 is present at a concentration selected to achieve a consumer's desired cosmetic shade effect with a processing time of about 5 minutes, and wherein the at least one hair refreshing composition that demonstrates stability.

17. The process according to claim 16, further comprising at least one color treatment step prior to providing the at least one hair refreshing composition, wherein the hair is dyed or lightened.

18. The process according to claim 16, wherein the hair is blonde hair and wherein the violet toned direct dye comprising EXT. VIOLET 2 is present in the hair refreshing composition from about 0.1% to about 1% by weight based on the weight of the composition.

19. The hair refreshing composition according to claim 13, wherein the hair refreshing composition is free or essentially free of imidazolium-based compounds, ammonium-based compounds, and combinations thereof.

20. A hair refreshing composition comprising a color toning system comprising at least one direct dye comprising EXT. VIOLET 2, and an acidic bonding restorative base, wherein:
the acidic bonding restorative base comprises:
  at least one anionic surfactant comprising an isethionate surfactant;
  at least one ester comprising coco-caprylate/caprate;

at least one cationic compound selected from the group consisting of polysaccharide-based cationic compounds, cationic silicone compounds, and combinations thereof;

at least one emulsifier, at least one additional surfactant selected from the group consisting of non-ionic surfactants, amphoteric surfactants and combinations thereof; and water;

the hair refreshing composition is free or essentially free of imidazolium-based compounds, ammonium-based compounds, and combinations thereof;

the hair refreshing composition excludes HC VIOLET NO. 2, BASIC VIOLET 2, HC BLUE NO. 2, and BASIC RED 51;

EXT. VIOLET 2 is present in the hair refreshing composition from about 0.1% to about 2% by weight based on the total weight of the hair refreshing composition; and the hair refreshing composition has a pH in a range from about pH 5.3 to about pH 5.9.

* * * * *